(12) United States Patent
Sohn et al.

(10) Patent No.: US 8,377,676 B2
(45) Date of Patent: Feb. 19, 2013

(54) MUTATED NUCLEOTIDE SEQUENCES OF BATROXOBIN, MUTATED α FACTOR SECRETION SIGNAL SEQUENCE AND PROCESSES FOR PREPARING BATROXOBIN USING THE SAME

(75) Inventors: Young-Doug Sohn, Yongin-si (KR); Bum Joon Kim, Seoul (KR); Ok Hwan Kim, Seoul (KR); Kyoung Jun Kim, Seoul (KR); Ji Hun Shin, Seoul (KR); Sung Yu Hong, Seoul (KR); Jae Hoon Hwang, Seoul (KR); Kwang Hoe Chung, Seongnam-si (KR)

(73) Assignee: Biobud Co., Ltd, Seoul (KR)

( * ) Notice: Subject to any disclaimer, the term of this patent is extended or adjusted under 35 U.S.C. 154(b) by 236 days.

(21) Appl. No.: 12/810,902

(22) PCT Filed: Dec. 23, 2008

(86) PCT No.: PCT/KR2008/007605
§ 371 (c)(1),
(2), (4) Date: Oct. 8, 2010

(87) PCT Pub. No.: WO2009/084841
PCT Pub. Date: Jul. 9, 2009

(65) Prior Publication Data
US 2011/0136207 A1  Jun. 9, 2011

(30) Foreign Application Priority Data
Dec. 28, 2007 (KR) .................. 10-2007-0139776

(51) Int. Cl.
*C12N 9/74* (2006.01)
*C12N 15/57* (2006.01)

(52) U.S. Cl. ............. 435/214; 435/219; 435/320.1; 536/23.2

(58) Field of Classification Search .............. None
See application file for complete search history.

(56) References Cited

FOREIGN PATENT DOCUMENTS

| JP | 63-049084 A | 3/1988 |
|---|---|---|
| JP | 02-124092 A | 5/1990 |
| WO | WO 2005/045022 A1 | 5/2005 |

OTHER PUBLICATIONS

Itoh et al., "Molecular Cloning and Sequence Analysis of cDNA for Batroxobin, a Thrombin-Like Snake Venom Enzyme," J. Biol. Chem. 262:3132-3135, 1987.
NCBI GenBank Accession No. AAA18405.1, alpha-1 mating factor, Apr. 13, 2000.
NCBI GenBank Accession No. E01526.1, DNA encoding Batroxobin, Nov. 4, 2005.
International Search Report from International Application No. PCT/KR2008/007605, dated Aug. 5, 2009 (date of completion of search) and Aug. 6, 2009 (date of mailing of report).

*Primary Examiner* — Rebecca Prouty
(74) *Attorney, Agent, or Firm* — Clark & Elbing LLP

(57) ABSTRACT

The present invention relates to a batroxobin-encoding nucleotide sequence and/or a mutated α-factor secretion signal sequence, and a vector and a transformant using the same. The batroxobin-encoding nucleotide sequence of this invention exhibits an excellent expression efficiency in yeast, particular *Pichia pastoris* and the recombinant batroxobin is obtained at 4-13 fold higher yield than natural-occurring batroxobin-encoding sequences. The protein expression system which uses the batroxobin-encoding nucleotide sequence as well as mutated α-factor secretion signal peptide sequence of this invention obtains the recombinant batroxobin at about 20-fold higher yield than natural-occurring batroxobin-encoding sequences. In addition, the recombinant batroxobin prepared using the sequence of this invention has a significantly plausible activity and stability compared with natural-occurring batroxobin.

3 Claims, 10 Drawing Sheets columns: 1. native  5. BatSMx
2. rbat  6. SMFBatMd
3. BatMd  7. SMFBatMx
4. BatMx  8. SMFBatSMx

MUTATED NUCLEOTIDE SEQUENCES OF BATROXOBIN, MUTATED α FACTOR SECRETION SIGNAL SEQUENCE AND PROCESSES FOR PREPARING BATROXOBIN USING THE SAME

CROSS-REFERENCE TO RELATED APPLICATIONS

This application is the U.S. national stage filing under 35 U.S.C. §371 of international application PCT/KR2008/007605, filed Dec. 23, 2008, which claims benefit of Korean Patent Application 10-2007-0139776, filed Dec. 28, 2007.

BACKGROUND OF THE INVENTION

1. Field of the Invention

The present invention relates to a batroxobin-encoding nucleotide sequence and/or a mutated α-factor secretion signal sequence containing a specific sequence, and a vector and a transformant using the same.

2. Background of Technique

Generally, venom effect on blood coagulation cascade and fibrinolytic pathway of mammalian including human has been investigated for a long time and several effective agents have been isolated and characterized. Various components included in venom are known to affect fibrin-clotting, platelet aggregation and so on directly or indirectly, thus to be used as pro-coagulant or anti-coagulant (Meaume, *J. Toxicon*, 4: 2558 (1966); Matsui et al., *Biochim. Biophys. Acta.*, 1477: 146-156 (2000)). Some of the components are already characterized and broadly used for diagnosis and therapy of thrombosis. In particular, the study about thrombin-like enzyme converting fibrinogen into fibrin by cleavage of fibrinopeptide has been performed actively and over 20 proteins have been reported, and cDNA of some was characterized.

The thrombin-like enzyme initially hydrolyze fibrinopeptide A of fibrinogen molecule to make unstable fibrin clot (des-A-fibrin) unlike thrombin, mammalian native blood coagulation protein, but the unstable fibrin clot is rapidly degraded by in vivo fibrinolysis system over time to eventually decrease blood fibrinogen level (Pirkle, H., and Stocker, K. *Thromb. Haemost.*, 65: 444-450 (1991); Marsh, N. A., *Blood Coagul. Fibrinolysis*, 5: 339-410 (1994)).

Therefore, the thrombin-like enzyme is used in clinic field as hemostatic agent or therapeutic and preventing agent for thrombosis by using these both-sided characteristics of enzyme. This enzyme don't also have an influence on other blood coagulation factors and activation of platelet, with which merit it shows effective hemostatic activity to intravenously or intramuscularly inject the small amount of the enzyme (2 NIH unit/60 kg) 1-2 hrs before surgery. On the other hand, it is possible to reduce blood fibrinogen level without side effects such as bleeding, that can be happen when using thrombolytic enzyme, by controlling dose and administration time of enzyme. The release of des-A-fibrin and FDP (fibrinogen degradation products) formed during the above process stimulate heoendothelial cell to induce the production of plasminogen activator. The enzyme is used as therapeutic and preventing agent for thrombosis because the enzyme can inhibit thrombin activity (Schumacher et al., *Thromb. Res.*, 81: 187-194 (1996); and Bell W. R. Jr., *Drugs*, 54: 18-30 (1997)).

Recently, this fibrinogen reduction effect of the thrombin-like enzyme is reported to be feective on therapy of heparin-induced thrombocytopenia or acute ischemic stroke caused by administration of heparin (Dempfle et al., *Blood*, 96: 2793-2802 (2000)).

The clinically used all thrombin-like enzymes are native proteins isolated and purified from venom. Batroxobin isolated from venom of Latin venomous snake *Bothrops atrox moojeni* is commercially available from Italian Solco Basle Ltd. Company and Swiss Pentapharm Company and is sold as trade names like reptilase (for hemostasis), defibrase (fro thrombolysis), reptilase-reagent (for diagnosis reagent). Botropase (for hemostasis, Italian Ravizza Company) isolated from venom of Latin venomous snake *Bothrops jararaca*, Malayan pit viper and Ancrod (American Knoll Pharmaceutical Company) isolated from venom of *Calloselasma rhodostoma* are also commercially available.

Recently, Vivostat System (Denmark, Vivosolution Co.) using batroxobin as an autologous fibrin sealant with the purpose of bleeding prevention and suture in surgical operation also is in the limelight.

Likewise, the method to produce recombinant protein has been intensively studied by various researchers since massive production batroxobin purified from snakes was limited. In the investigation to express protein from eukaryote in microorganisms, protein expression is reduced due to gene codons with low translation efficiency of *E. coli* (prokaryote) in the translation after transcription of eukaryotic genes. To overcome it, the method to improve protein translation is commonly carried out by using a recombinant *E. coli* strain into which foreign eukaryotic tRNA gene is transformed to recognize amino acid codon with low frequency in *E. coli*. Notwithstanding these efforts, inactive proteins are produced during refolding process of proteins expressed in *E. coli* (Yang et al., *Biotechnol. Lett.*, 25: 101-104 (2003); Fan et al., *Biochem. Mol. Biol. Int.*, 47: 217-225 (1999); Maeda et al., *J. Biochem.*, 109: 632-637 (1991)). As reported until now, any successful case in which recombinant thrombin-like enzyme is expressed in *E. coli* and then has similar activity compared with specific activity of nature enzyme is not reported yet.

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THE INVENTION

The present inventors have made intensive studies to develop an expression system of a recombinant batroxobin at a high yield in yeast, particularly the genus *Pichia*. As results, we have discovered that the biologically active recombinant batroxobin could be collected at higher yield by using mutated batroxobin cDNAs or mutated α-factor leader peptide-encoding nucleotide sequences.

Accordingly, it is an object of this invention to provide a batroxobin-encoding nucleotide sequence.

It is another object of this invention to provide a vector comprising the nucleotide sequences.

It is still another object of this invention to provide a transformant transformed by the vector.

It is further object of this invention to provide a preparation method of a recombinant batroxobin.

It is still further object of this invention to provide an α-factor secretion signal peptide-encoding nucleotide sequence.

It is another object of this invention to provide a vector comprising the nucleotide sequences.

It is still another object of this invention to provide a transformant transformed by the vector.

It is further object of this invention to provide a preparation method of a recombinant batroxobin.

Other objects and advantages of the present invention will become apparent from the following detailed description together with the appended claims and drawings.

In one aspect of this invention, there is provided a batroxobin-encoding nucleotide sequence comprising the nucleotide sequences of SEQ IDs NO:3, NO:5 or NO:7.

The present inventors have made intensive studies to develop an expression system of a recombinant batroxobin at a high yield in yeast, particularly the genus *Pichia*. As results, we have discovered that the biologically active recombinant batroxobin could be collected at higher yield by using mutated batroxobin cDNAs or mutated α-factor leader peptide-encoding nucleotide sequences.

The nucleotide sequence of SEQ IDs NO:3, NO:5 or NO:7 represented in this invention includes the nucleotide sequences to express batroxobin at a high yield in yeast, preferably in microorganisms involved in the genus *Pichia* and most preferably in *Pichia pastoris*.

The term "nucleotide sequence" used herein refers to analogues with modified sugar or base as well as natural nucleotides (Scheit, *Nucleotide Analogs*, John Wiley, New York (1980); Uhlman and Peyman, *Chemical Reviews,* 90: 543-584 (1990)).

According to a preferable embodiment, the nucleotide sequence of this invention SEQ IDs NO:5 or NO:7 and most preferably SEQ ID NO:7.

As illustrated in the Examples below, the recombinant batroxobin is obtained at 4-13 fold yield by using the nucleotide sequence of this invention compared with natural-occurring batroxobin-encoding sequence.

In another aspect of this invention, there is provided a vector comprising batroxobin-encoding nucleotide sequences described above.

The vector system of this invention may be constructed by various methods known to those skilled in the art which are disclosed in Sambrook et al., Molecular Cloning, A Laboratory Manual, Cold Spring Harbor Laboratory Press (2001), which is herein incorporated by reference.

Typically, the vector of this invention may be constructed as cloning or expression vector. The vector of the present invention utilizes yeast, preferably in microorganisms involved in the genus *Pichia* and more preferably in *Pichia pastoris* as a host.

Using yeast like *Pichia pastoris* as a host, the vector of this invention utilizes a promoter of genes such as alcohol oxidase 1 (AOX1), alcohol oxidase 2 (AOX2), 3-phosphoglycerate kinase, enolase, glyceraldehyde-3-phosphaste dihydrogenase, hexokinase, pyruvate decarboxylase, phosphofructokinase, glucose-6-phosphate isomerase, 3-phosphoglycerate mutase or pyruvate kinase, and most preferably the promoter of alcohol oxidase 1 (AOX1).

To purify batroxobin expressed from the vector of this invention in an easy manner, other sequences could be fused with it. For example, a fused sequence includes glutathione-S-transferase (Pharmacia, USA), maltose-binding protein (NEB, USA), FLAG (IBI, USA) and 6×His (hexahistidine; Quiagen, USA) and so on. Because of the additive sequences for purification, a protein expressed in the host is purified by an affinity chromatography in a high-throughput and easy manner.

On the other hand, the expression vector of this invention includes an antibiotics-resistance gene known to those ordinarily skilled in the art as a selection marker, for example resistant genes against ampicillin, gentamycin, carbenicillin, chloramphenicol, streptomycin, kanamycin, neomycin and tetracycline.

According to a preferable embodiment, the vector of the present invention includes a secretion signal peptide-encoding nucleotide sequence. More preferably, the vector of the present invention includes α-factor secretion signal peptide-encoding nucleotide sequence as the secretion signal peptide and most preferably α-factor secretion signal peptide-encoding nucleotide sequence mutated from SEQ ID NO:11.

According to a preferable embodiment, the vector of the present invention is a vector with a gene map of FIG. 19. Preferably, ColE1 represents a pBR322-derived replication origin in FIG. 19 and an ampicillin-resistant gene of *E. coli* and a histidine amino acid biosynthesis gene (His4) of yeast are used as the selection marker and a promoter gene is derived from alcohol oxidase 1 (AOX1) gene of yeast. Batroxobin gene includes the nucleotide sequence of SEQ IDs NO:3, NO:5 or NO:7 and α-factor secretion signal sequence includes α-factor secretion signal peptide sequence mutated from SEQ ID NO:11.

In still another aspect of this invention, there is provided a transformant transformed by the vector containing a batroxobin-encoding nucleotide sequence.

The host cells in which the present vector is stably and successively cloned and expressed, also utilize any one of yeast cells known to those skilled in the art, for example *Pichia pastoris, Pichia methanolica, Hansenula polymorpha, Saccharomyces cerevisiae* and *Shizosaccharomyces pombae.*

Most preferably, the host cells used in this invention is *Pichia pastoris. Pichia pastoris* a kind of methylotrophic yeast and has some advantages of: (i) rapid and convenient growth in the medium with low-cost, (ii) massive expression of proteins. In the vector containing AOX1 promoter, protein expression is strongly induced by addition of methanol to medium. In the vector containing α-factor secretion signal peptide, protein purification is easily carried out by secretion of desired batroxobin into medium.

The system delivering the present vector into host cells includes $CaCl_2$ method (Cohen, S. N. et al., *Proc. Natl. Acac. Sci. USA,* 9: 2110-2114 (1973)), Hanahan method (Cohen, S. N. et al., *Proc. Natl. Acac, Sci. USA,* 9: 2110-2114 (1973); and Hanahan, D., *J. Mol. Biol.,* 166: 557-580 (1983)), microinjection (Capecchi, M. R., *Cell,* 22: 479 (1980)), calcium phosphate precipitation (Graham, F. L. et al., *Virology,* 52: 456 (1973)), electroporation (Neumann, E., et al., *EMBO J.,* 1: 841 (1982)), liposome-mediated transfection (Wong, T. K. et al., *Gene,* 10: 87 (1980)), DEAE-dextran treatment (Gopal, *Mol. Cell Biol.,* 5: 1188-1190 (1985)) and gene bombardment (Yang et al., *Proc. Natl. Acad. Sci.,* 87: 9568-9572 (1990)).

In still another aspect of this invention, there is provided a preparation method of a recombinant batroxobin, comprising the steps of: (a) transforming a host cell using the present vector; and (b) culturing the transformed cell to provide the recombinant batroxobin.

The culture of transformed cells could be carried out by various methods known to those skilled in the art. The detailed description to culture and fermentation of microorganisms is disclosed in Kubitschek, H. E., Introduction to Research with Continuous Cultures. Englewood Cliffs, N.J.: Prentice-Hall, Inc., 1970; Mandelstam, J., et al., Biochemistry of Bacterial Growth, 3rd ed. Oxford: Blackwell, 1982; Meynell, G. G., et al., Theory and Practice in Experimental Bacteriology, 2nd ed. Cambridge: Cambridge University Press, 1970; and Gerhardt, P., ed., Manual of Methods for General Bacteriology, Washington: *Am. Soc. Microbiol,* 1981, which are herein incorporated by reference.

For instance, the transformed cells are cultured in BMG (buffered minimal glycerol) liquid media by inoculation and batroxobin protein expression through AOX1 promoter is induced by adding methanol to media where cell density reaches at predetermined point, obtaining batroxobins secreted into media.

Batroxobin secreted into media is collected in a purified form according to various purification methods known to those skilled in the art. For example, batroxobin is obtained in a purified form using purification methods such as solubility fractionation using ammonium sulfate, size fractionation filtration (ultrafiltration) and various chromatographies (separation using size, charge, hydrophobicity or affinity).

In one aspect of this invention, there is provided a α-factor secretion signal peptide-encoding nucleotide sequence consisting of the nucleotide sequences of SEQ ID NO:11.

The α-factor secretion signal peptide-encoding nucleotide sequence consisting of the nucleotide sequence of SEQ IDs NO:11 includes the nucleotide sequences to express a protein at a high yield rate in yeast, preferably in microorganisms involved in the genus *Pichia* and most preferably in *Pichia pastoris*.

The term "nucleotide sequence" used herein refers to analogues with modified sugar or base as well as natural nucleotides (Scheit, *Nucleotide Analogs*, John Wiley, New York (1980); Uhlman and Peyman, *Chemical Reviews,* 90: 543-584 (1990)).

As illustrated in the Examples below, the recombinant protein (e.g., batroxobin) is obtained at about 2-3 times higher production by using the nucleotide sequence of this invention compared with natural α-factor secretion signal peptide-encoding sequence.

In another aspect of this invention, there is provided a vector comprising the nucleotide sequence containing a mutated α-factor secretion signal.

The vector system of this invention may be constructed by various methods known to those skilled in the art which are disclosed in Sambrook et al., Molecular Cloning, A Laboratory Manual, Cold Spring Harbor Laboratory Press (2001), which is herein incorporated by reference.

Typically, the vector of this invention may be constructed as cloning or expression vector. The vector of the present invention utilizes yeast, preferably in microorganisms involved in the genus *Pichia* and more preferably in *Pichia pastoris* as a host.

Using yeast like *Pichia pastoris* as a host, the vector of this invention utilizes a promoter of genes such as alcohol oxidase 1 (AOX1), alcohol oxidase 2 (AOX2), 3-phosphoglycerate kinase, enolase, glyceraldehyde-3-phosphaste dihydrogenase, hexokinase, pyruvate decarboxylase, phosphofructokinase, glucose-6-phosphate isomerase, 3-phosphoglycerate mutase or pyruvate kinase, and most preferably the promoter of alcohol oxidase 1 (AOX1) and most preferably the promoter of alcohol oxidase 1 (AOX1) gene.

To purify a protein expressed from the vector of this invention in an easy manner, other sequences could be fused with it. For example, a fused sequence includes glutathione-S-transferase (Pharmacia, USA), maltose-binding protein (NEB, USA), FLAG (IBI, USA) and 6×H (hexahistidine; Quiagen, USA) and so on. Because of the additive sequences for purification, the protein expressed in the host is purified by an affinity chromatography in a high-throughput and easy manner.

On the other hand, the expression vector of this invention includes an antibiotics-resistance gene known to those ordinarily skilled in the art as a selection marker, for example resistant genes against ampicillin, gentamycin, carbenicillin, chloramphenicol, streptomycin, kanamycin, neomycin and tetracycline.

The proteins expressed by the present vector is not particularly restricted and include hormones, hormone analogues, enzymes, enzyme inhibitors, signal transduction proteins or their parts, antibodies or their parts, monoclonal antibody, binding proteins or their binding domains, antigens, adhesion proteins, structure proteins, regulatory proteins, toxic proteins, cytokines, transcription factors, blood coagulation factors and plant defense-related proteins, but not limited to. Preferably, the protein expressed by the present vector is batroxobin.

Preferably, the nucleotide sequence of SEQ IDs NO:1, NO:3, NO:5 or NO:7 is used as a batroxobin-encoding sequence, more preferably that of SEQ IDs NO:3, NO:5 or NO:7 and most preferably that of SEQ IDs NO:5 or NO:7 in the present vector used in batroxobin expression. The nucleotide sequence of SEQ IDs NO:3, NO:5 or NO:7 is to express batroxobin at a high yield rate in yeast, preferably in microorganisms involved in the genus *Pichia* and most preferably in *Pichia pastoris*.

According to a preferable embodiment, the vector of the present invention is a vector with a gene map of FIG. 19. Preferably, ColE1 represents a pBR322-derived replication origin in FIG. 19 and an ampicillin-resistant gene of *E. coli* and a histidine amino acid biosynthesis gene (His4) of yeast are used as the selection marker and a promoter gene is derived from alcohol oxidase 1 (AOX1) gene of yeast. Batroxobin gene includes the nucleotide sequence of SEQ IDs NO:1, NO:3, NO:5 or NO:7 and α-factor secretion signal sequence includes α-factor secretion signal peptide sequence mutated from SEQ ID NO:11.

In still another aspect of this invention, there is provided a transformant transformed by the vector described above.

The host cells in which the present vector is stably and successively cloned and expressed, also utilize any one of yeast cells known to those skilled in the art, for example *Pichia pastoris, Pichia methanolica, Hansenula polymorpha, Saccharomyces cerevisiae* and *Shizosaccharomyces pombae*.

Most preferably, the host cells used in this invention is *Pichia pastoris. Pichia pastoris* is a kind of methylotrophic yeast and has some advantages of: (i) rapid and convenient growth in the medium with low-cost, (ii) massive expression of proteins. In the vector containing AOX1 promoter, protein expression is strongly induced by addition of methanol to medium. In the vector containing α-factor secretion signal peptide, protein purification is easily carried out by secretion of desired batroxobin into medium.

The system delivering the present vector into host cells includes CaCl$_2$ method (Cohen, S. N. et al., *Proc. Natl. Acac. Sci. USA,* 9: 2110-2114 (1973)), Hanahan method (Cohen, S. N. et al., *Proc. Natl. Acac. Sci. USA,* 9: 2110-2114 (1973); and Hanahan, D., *J. Mol. Biol.,* 166: 557-580 (1983)), microinjection (Capecchi, M. R., *Cell,* 22: 479 (1980)), calcium phosphate precipitation (Graham, F. L. et al., *Virology,* 52: 456 (1973)), electroporation (Neumann, E., et al., *EMBO J.,* 1: 841 (1982)), liposome-mediated transfection (Wong, T. K. et al., *Gene,* 10: 87 (1980)), DEAE-dextran treatment (Gopal, *Mol. Cell Biol.,* 5: 1188-1190 (1985)) and gene bombardment (Yang et al., *Proc. Natl. Acad. Sci.,* 87: 9568-9572 (1990)).

In still another aspect of this invention, there is provided a preparation method of a recombinant batroxobin, comprising the steps of: (a) transforming a host cell using the present vector; and (b) culturing the transformed cell to provide the recombinant batroxobin.

The culture of transformed cells could be carried out by various methods known to those skilled in the art. The detailed description to culture and fermentation of microorganisms is disclosed in Kubitschek, H. E., Introduction to Research with Continuous Cultures. Englewood Cliffs, N.J.: Prentice-Hall, Inc., 1970; Mandelstam, J., et al., Biochemistry of Bacterial Growth, 3rd ed. Oxford: Blackwell, 1982; Meynell, G. G., et al., Theory and Practice in Experimental Bacteriology, 2nd ed. Cambridge: Cambridge University Press, 1970; and Gerhardt, P., ed., Manual of Methods for General Bacteriology, Washington: *Am. Soc. Microbiol*, 1981, which are herein incorporated by reference.

For instance, the transformed cells are cultured in BMG (buffered minimal glycerol) liquid media by inoculation and protein expression through AOX1 promoter is induced by adding methanol to media where cell density reaches at predetermined point, obtaining proteins secreted into media.

Proteins secreted into media are collected in a purified form according to various purification methods known to those skilled in the art. For example, proteins are obtained in a purified form using purification methods such as solubility fractionation using ammonium sulfate, size fractionation filtration (ultrafiltration) and various chromatographies (separation using size, charge, hydrophobicity or affinity).

The features and advantages of this invention are summarized as follows:

(i) the batroxobin-encoding nucleotide sequence of this invention exhibits an excellent expression efficiency in yeast, particular *Pichia pastoris* and the recombinant batroxobin is obtained at 4-13 fold higher yield than natural-occurring batroxobin-encoding sequences.

(ii) mutated α-factor secretion signal peptide sequences of this invention also are responsible for about 2-3 times higher production of recombinant batroxobins.

(iii) therefore, the protein expression system which uses the batroxobin-encoding nucleotide sequence as well as mutated α-factor secretion signal peptide sequence of this invention obtains the recombinant batroxobin at about 20-fold higher yield than natural-occurring batroxobin-encoding sequences.

(iv) the recombinant batroxobin prepared using the sequence of this invention has an excellent activity compared with natural-occurring batroxobin.

(v) the recombinant batroxobin prepared using the sequence of this invention has an significantly plausible stability.

BRIEF DESCRIPTION OF THE DRAWINGS

In FIG. 1 and FIG. 2, each lane is as follows: lane 1, control (pPIC-rBat containing natural cDNA); lane 2, mutated recombinant clone (pBatMd); lane 3, pBatMx; lane 4, pBatSMx; lane M, molecular size marker; lane 5, secretion signal SMF-substituted natural rbat; lane 6, SMFbatMd; lane 7, SMFBatMx; and lane 8, SMFBatSMx.

FIG. 4 and FIG. 5 is phenyl-sepharose and heparin-sepharose chromatogram, respectively. The recombinant batroxobin is prepared by using a SMFBatSMx gene. Arrowhead indicates a fraction containing the highest amount of recombinant batroxobin.

Figure 1:
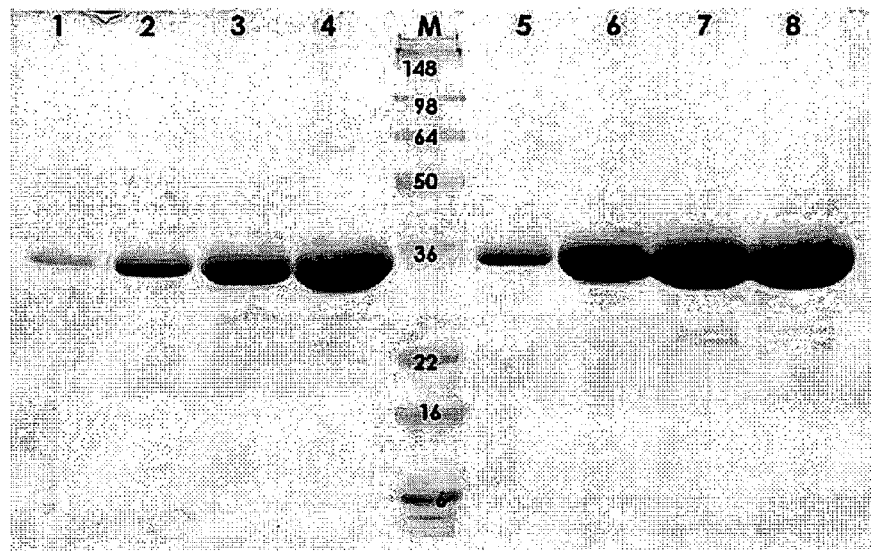
FIG. 1 represents SDS-PAGE (sodium dodecyl sulfate-polyarcylamide gel electrophoresis) comparing the expression of natural batroxobin cDNA and mutated cDNA of the present invention.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Venom-Derived Natural Batroxobin cDNA Cloning

The catalytic domain of mature form batroxobin of *Bothrops atrox moojeni* was obtained from GSrBAT strains containing pPIC-rBat vector (Patent Appl. Publ. No. 2007-4541, Korean Culture Center of Microorganisms, Deposit No. KCCM-10522), a yeast expression vector to express the natural batroxobin of the present invention. The catalytic domain includes Xho I/KEX2-Not I 716 bp fragments composed of 696 bp coding region sequence of 231 amino acids (from valine ($1^{st}$ codon, GTC) to proline (231 codon, CCG)) and additive base sequence of 20 bp. The fragment was amplified by PCR reaction using forward primer (A5') 5'-ctcgagaaaa-gagtcattggaggtgatg-3' and reverse primer (Not I) 5'-gcggc-cgctcatgggcaagtagcag-3'. Temperature cycles of PCR amplification is following as: denaturing at 94° C. for 1.5 min, annealing at 52° C. for 1 min, elongating at 72° C. for 1.5 min, 30 cycles. PCR products were electrophoresized on 1% agarose gel and 716 bp of DNA fragments were purified and then subcloned into pGEMT-Easy vector (Promega, USA), which was confirmed by sequencing. The gene sequence of subcloned natural batroxobin is described in SEQ ID NO:1.

Based on the natural batroxobin cDNA sequence, mRNA structure and codon usage were analyzed in yeast, *Pichia pastoris*. The number of codon having low translation efficiency of not more than 10% was 15 in yeast, corresponding to 6.4% of whole sequence and that of not more than 20% was 42, corresponding to 18.1% of whole sequence. Thus, the whole percentage corresponding to 52 amino acid codons of not more than 20% was 24.6%. In more detail, codons having translation efficiency of not more than 10% were argine (CGG/CGC), alanine (GCG), leucine (CTC), serine (AGC), glycine (GGG) and proline (CCG), and codons having translation efficiency of not more than 20% included argine (CGT), isoleucine (ATA), valine (GTA/GTG), threonine (ACG), proline (CCC), glycine (GGC), leucine (TTA/CTG/CTT) and serine (AGT). In addition, AG value permits to presume a potential secondary hairpin-loop structure of mRNA during translation and AG value of natural batroxobin was −128.3 kcal/mol.

Example 2

Gene Modification to Enhance Protein Translation Efficiency of Venom-Derived Natural Batroxobin cDNA Mutagenesis was carried out to enhance protein translation efficiency of venom-derived natural batroxobin cDNA.

716 bp of DNA fragments containing natural batroxobin cDNA described in Example 1 were used as a template. Then, 155 bp of Xho I-EcoR I fragment was amplified by using primer sets (forward primer (A5'), 5'-ctcgagaaaagagtcattggaggtgatg-3'; reverse primer (A3'), 5'-gtgaattctcataaatctcctgt-tacagtgtgc-3') and 312 bp of EcoR I-Hind III fragment was amplified by using primer sets (forward primer (B5'), 5'-gaat-tcacttgggtaaacatgccggaagtgtagca-3'; reverse primer (B3'), 5'-gtaagcttcacgacacaccgtattat-3'). Temperature cycles of PCR amplification is the same to the Example 1. During PCR reaction, the natural 5'-CGCATACACCTT-3' nucleotide sequence which encodes Arg48, Ile49 and Leu51 is substituted into 5'-AGAATTCACTTG-3' nucleotide sequence containing EcoR I-recognition sequence which is preferred in yeast (*Pichia pastoris*). In addition, batroxobin gene is separated into 155 bp of Xho I-EcoR I fragment, 312 bp of EcoR I-HindIII fragment and 250 bp of Hind III-Not I fragment. The sequencing and additive mutagenesis were carried out by subcloning these fragments into pGEMT-Easy vector (Promega. USA) or pUC118HincII/BAP vector (Takara Bio Inc, JAPAN). The Arg23 (cgg) codon sequence was substituted into other Arg codon sequence (aga) by mutagenesis PCR reaction using 155 bp of Xho I-EcoR I fragment subcloned into pGEMT-Easy vector as a template and primer sets (forward primer (M1), 5'-actactctcctagatatttctgtggtat-gactttga-3'; reverse primer (M2), 5'-cagaaatatctaggagagtagta-catgaatgc-3'). Each Ala103 (gcg), Pro104 (cct), Leu105 (ctc) and Ser106 (agc) codon sequence was substituted into other Ala (gct), Pro104 (cca), Leu105 (ttg) and Ser106 (tct) codon sequence (aga) by mutagenesis PCR reaction using 312 bp of EcoR I-Hind III fragment subcloned into pGEMT-Easy vector as a template and primer sets (forward primer (M3), 5'-caaagacaaaggagcgatgtgttcactggacag-3'; reverse primer (M4), 5'-acatcgctcctttgtctttgccttccaaccctccagt-3').

Finally, to induce mutagenesis in 250 bp of Hind III-Not I fragment having low codon efficiency of its C-terminal in yeast, each forward and reverse oligonucleotide linker primer sets was synthesized and mixed at an equal concentration. The mixture (DNA and primer sets) were denatured at 95° C. for 5 min and annealed at room temperature. The primer reactants were phosphorylated by T4 polynucleotide kinase (PNK) enzyme (Takara Bio Inc, JAPAN) and then T4 DNA ligation reaction was performed according to order of primer sets. The nucleotide sequences of primer sets were used as follows:

C1F,
5'-agcttacaatggtttgccagctaaaacattgtgtgcaggtgtcttg caa-3',

C1R,
5'-ctccttgcaagacacctgcacacaatgttttagctggcaaaccatt gta-3';

C2F,
5'-ggaggtattgatacatgtggtggtgactctggtggacctttgatct gta-3',

C2R,
5'-ccattacagatcaaaggtccaccagagtcaccaccacatgtatcaa tac-3';

C3F,
5'-atggacaattccagggtattttgtcttggggatctgatccttgtgc cg-3',

C3R,
5'-ggttcggcacaaggatcagatccccaagacaaaatacccctggaatt gt-3';

C4F,
5'-aaccaagaaagcctgccttctacaccaaggtctttgattatttgcc ttg-3',

C4R,
5'-gatccaaggcaaataatcaaagaccttggtgtagaaggcaggcttt ctt-3';
and

DF,
5'-gatccagtctattattgcaggaaataaaactgctacttgcccatga gc-3',

DR,
5'-ggccgctcatgggcaagtagcagttttatttcctgcaataatagac tg-3'.

250 bp of Hind III-Not I fragment was amplified by PCR reaction using the ligation product described above as a template and primer sets (forward primer (C5'), 5'-aagcttacaatg-gtttgcca-3'; reverse primer (Not I), 5'-gcggccgctcatgggcaag-tagcag-3') and cloned into the Hind III site of pUC118HincII/BAP vector. Consequently, Gly156, Pro158, Ala159, Leu167, Gly170, Asp171, Gly175, Gly179, Pro181, Leu182, Gly190, Leu192, Ser196, Pro198, Pro202, Arg203, Leu215, Pro216, Ser220, Ala228 and Pro231 codon sequences of C-terminal of batroxobin were substituted into other codon sequences having high transcription efficiency, which was confirmed by sequencing.

As described above, the recombinant batroxobin gene was sequentially divided into three fragments (Xho I-EcoR I fragment, EcoR I-Hind III fragment and Hind III-Not I fragment) from 5'-terminal, which were subcloned into a gene cassette according to the sequence of restriction enzyme, generating a batroxobin mutated gene, BatMd (SEQ ID NO:3). Based on BatMd substituted codons having efficiency of not less than 10% for all codons having efficiency of not more than 10% in natural batroxobin gene, gene codon variants were further synthesized. Using BatMd-mutated sequence, all codons having efficiency of not more than 20% were substituted into those having efficiency of not less than 20%, generating BatMx (SEQ ID NO:5) and all codon having low efficiency were substituted into those theoretically having the highest efficiency in yeast, resulting in BatSMx (SEQ ID NO:7) which has the most optimal codon nucleotide sequence.

Each batroxobin variant genes described above was subcloned into the site Xho I-Not I of pPIC9 (Invitrogen, Corp.) vector, a yeast expression vector, constructing pBatMd, pBatMx and pBatSMx.

Example 4

Gene Modification to Enhance Secretion Leader Peptide Translation Efficiency of *Pichia* Protein and Construction of Fusion Protein Cloning Vector The secretion leader peptide of yeast used to secrete the recombinant protein into cell culture media is derived from α-factor pheromone of *Saccharomyces cerevisiae*. Up to date, all α-factor secretion leader peptides used in commercial yeast expression vector system are composed of gene nucleotide sequences of *Saccharomyces cerevisiae*. Particularly, a heterologous yeast expression vector system such as *Pichia pastoris* includes a leader sequence (SEQ ID NO:9) composed of nucleotide sequences of *Saccharomyces cerevisiae*.

It was demonstrated that among 85 amino acids, the number of not more than 20% of codons is 19 and that of not more than 10% of codons is 7 bp analyzing codon utilization of the leader sequence using codons of *Pichia*. Secretion signal gene codon (genotech, Korea) were synthesized to substitute for *Saccharomyces*-derived secretion signal gene codon, which were named as SMF and its nucleotide sequence was described in SEQ ID NO:11. To fuse a desirable recombinant protein at C terminal of SMF, it was inserted into the multi-cloning site of pUC118HincII/BAP (Takara Bio Inc., JAPAN), which was named as pSMF. The nucleotide sequence of GTA-TCT-CTC-GAG encoding Val80-Ser81-Leu82-Glu83 was replaced with that of GTT-TCT-TTG-GAA in the senses that Xho I nucleotide sequence (CTC-GAG) used in the cloning site of C-terminal of natural α-factor leader secretion sequence to be conventionally commercialized encodes a Leu codon (CTC) with low transcription efficiency. And then, PCR reaction was performed by using SMF gene as a template and primer sets (SMF-R, 5'-TAACTCTTTTTTCCAAAGAAACACCT-TCTTCCTTTGCTGC-3'; SMF-F, 5'-GGATCCAAACGAT-GAGATTTCCAT-3'). SMF-R was used as C-terminal primer overlapped with N-terminal of batroxobin and SMF-F was used as N-terminal primer producing BamH I nucleotide sequence at N-terminal of recombinant SMF gene cassette. N-terminal-encoding nucleotide sequence of following batroxobin genes was designed using primers corresponding to overlap sequence (amino acid sequence: L E K R/V I G G D E) consistent with codons mutated at C-terminal of SMF. PCR reaction was performed by using each batroxobin variants as template and primer sets: aMd/Mx (5'-CTTTG-GAAAAAAGAGTCATTGGAGGTGATGAA-3') in batMd and barMx, and aSMx2(5'-CTTTGGAAAAAAGAGTTAT-TGGTGGTGATGAA-3') in batSMx was used as N-terminal extension primer, respectively; Md/Mx-R (5'GCGGCCGCT-CATGGGCAAGT-3') in batMd and barMx, and SMx-R (5'-GCGGCCGCTTATGGACAAGT-3') in batSMx was used as C-terminal primer, respectively. The resulting SMF and PCR products of batroxobin genes were mixed according to corresponding combinations, and N-terminal and C-terminal primers used in each SMF and batroxobin modification were added. Assembly PCR was performed and then subcloned into pTOP Blunt vector (Enzynomics™, Korea), constructing SMFBatMd/SMFBatMx/SMFSMx as gene cassette in which codons of α-secretion sequence of SMF and batroxobin gene are optimized. These genes was digested with BamH I-Not I retriction enzymes. BamH I-Not I fragments (970 bp) were recovered and subcloned into pPIC9, *Pichia* expression vector, generating expression vectors (i.e., pSMFrbat, pSMF-BatMd, pSMFBatMx and pSMFBatSMX).

Example 5

Comparison Expression of Between Natural cDNA and Mutated cDNA of Batroxobin

The vectors prepared in example 3 and 4 were transformed into *Pichia pastoris* strain (GS115, Invitrogen) under the voltage condition of 1.5 kV using an electroporator (Bio-Rad Gene Pulser, USA) and the transformants were inoculated on histidine-deficient YNB (yeast nitrogen base) solid medium. After that, selected single colony was inoculated into 1 L of BMG (Buffered Minimal Glycerol) liquid media (100 mM sodium phosphate (pH 6.0), 1.34% yeast nitrogen base, $4 \times 10^{-5}$% biotin, 1% glycerol) and incubated with shaking at 30° C. The expression of recombinant proteins via AOX1 (Alcohol Oxidase 1) promoter was induced by adding 0.1% methyl alcohol at 24 hrs interval in cell density in which the absorbance reached 1.0 at 600 nm. Yeast cells were removed by centrifugation, harvesting culture solution. Batroxobin expressed in yeast culture solution was purified as described in example 6 and each amount corresponding to the same culture volume was electrophoresized on SDS-PAGE. The gel was stained with Coomassie-brilliant Blue R-250. The expression was determined by production of a new protein band with a molecular weight of about 29-33 kDa (FIG. 1a) and also examined by Western blotting using antibody against batroxobin protein in the protein gel (FIG. 1b).

Likewise, the expression of protein was carried out and the expression amount of protein was compared. In FIGS. 1a-1b, each lane is as follows: lane 1, control (pPIC-rBat containing natural cDNA); lane 2, mutated recombinant clone (pBatMd); lane 3, pBatMx; lane 4, pBatSMx; lane M, molecular size marker; lane 5, secretion signal SMF-substituted natural rbat; lane 6, SMFbatMd; lane 7, SMFBatMx; and lane 8, SMFBatSMx. As shown in FIGS. 1a-1b, it was demonstrated that 33 kDa protein band corresponding to batroxobin protein was abundantly accumulated in mutated recombinant clones (e.g., BatMd, BatMx and BatSMx) than in natural gene (pPIC-rBat). The expression amount was increased according to the order of BatSMx, BatMx, BatMd. It was also demonstrated that much more amount of batroxobin was secreted into the culture solution by using mutated α-factor leader peptide.

Figure 2:
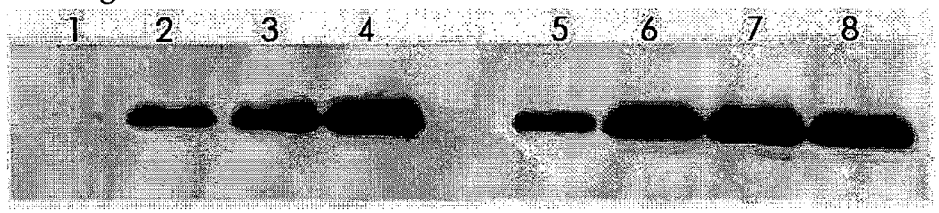
FIG. 2 represents Western blotting comparing the expression of natural batroxobin cDNA and mutated cDNA of the present invention.

On the other hand, glycosylation of expressed batroxobin protein was examined by deglycosylation reaction using endo-H enzyme (New England Biolab Inc., USA). This treatment resulted in the band shift of from 33 kDa to 26 kDa, demonstrating that the band is batroxobin protein (FIG. 2). In FIG. 2, intact batroxobin was detected and each lane is as follows: lane 1, natural rbat; lane 2, SMFBatMd; lane 3, SMFBatMx; land 4, SMFBatSMx; land 5, natural rbat; lane 6, SMFbatMd; lane 7, SMFBatMx; and lane 8, SMFBatSMx.

Each lane 5 to 8 was to treat endo-H in lane 1 to 4, representing band shift of protein by endo-H. As described above, it could be appreciated that the expression of recombinant batroxobin protein was increased in BatMd, BatMx and BatSMx (batroxobin-mutated cDNA), and SMF (secretion signal substituted) compared with natural gene.

Example 6

Purification of Recombinant Batroxobin

Figure 3:
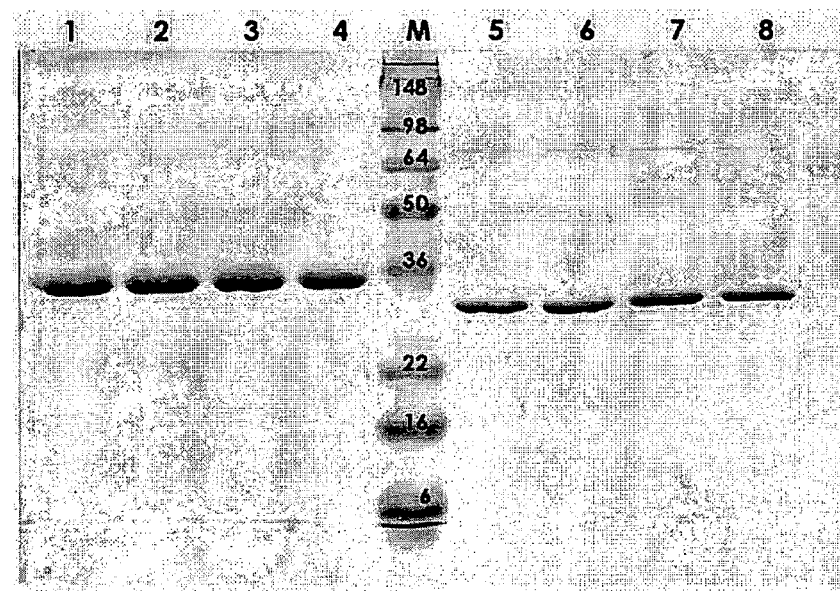
FIG. 3 represents SDS-PAGE treated with endo-H enzyme to examine glycosylation of a batroxobin protein. Each band of lane 1, lane 2, lane 3, lane 4 represents an intact batroxobin derived from natural rbat, SMFBatMd, SMFBatMx, SMF-BatSMx: lane 5, natural rbat; lane 6, SMFBatMd; lane 7, SMFBatMx; and lane 8, SMFBatSMx.
Figure 4:
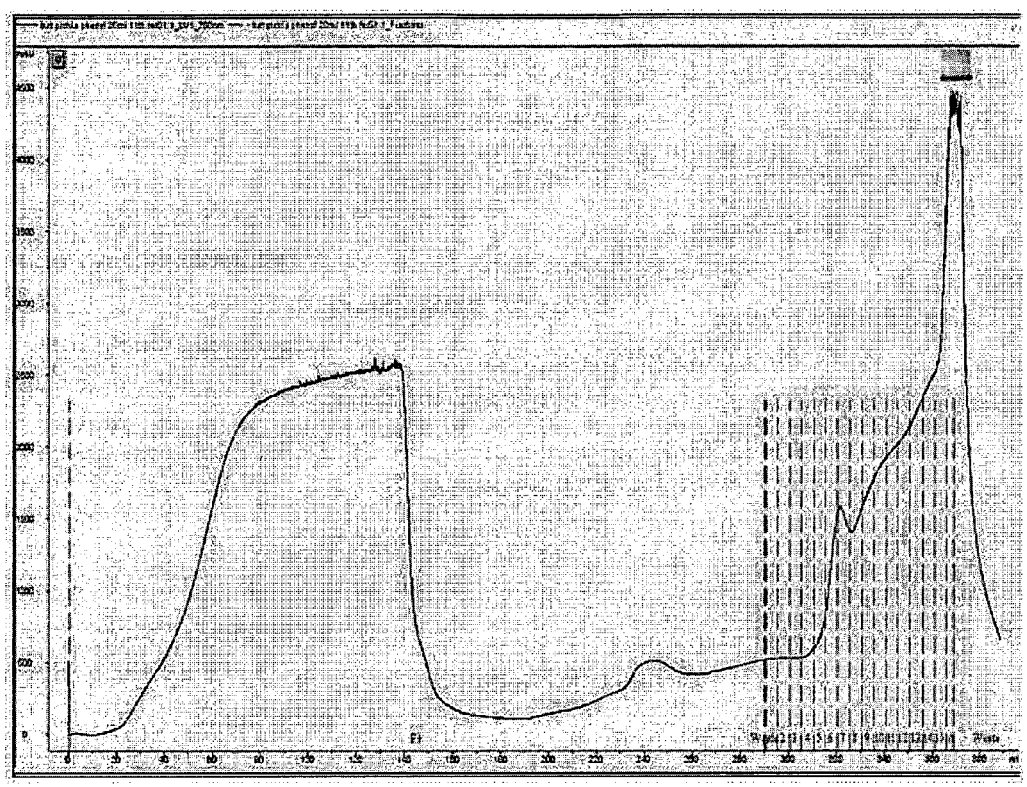
FIGS. 4-5 are chromatograms representing purification of a recombinant batroxobin.

Methanol-induced culture solution of yeast strain transformed with batroxobin expression vectors of example 5 was harvested by centrifuging at 5000×g and loaded into column (1.3×20 cm) packed with phenyl-sepharose (GE Healthcare, USA) equilibrated with 2.5 M ammonium sulfate solution. The fraction with enzyme activity of recombinant batroxobin was eluted at flow rate of 0.5 ml/min using a linear gradient of 0-2.5 M ammonium sulfate solution (FIG. 3a). The enzyme activity of recombinant batroxobin was measured according to the same method of example 1. The collected fractions with enzyme activity were dialyzed for 8 hrs (three times) in 20 mM Tris-HCl buffer (pH 7.5) and then were loaded into affinity column (heparin-sepharose column, 1×5 cm, GE Healthcare, USA) equilibrated with 20 mM Tris-HCl buffer (pH 7.5). The recombinant batroxobin was eluted with a linear gradient of 0-1 M the same buffered solution containing 1 M sodium chloride at the flow rate of 1 ml/min to get purely isolated recombinant thrombin-like enzyme (FIG. 3b). Each yield of BatMd, BatMx and BatSMx was increased 4.5-, 8.5- and 13-fold where the expression by natural batroxobin gene per 1 L culture solution was considered as 1. It was also demonstrated that each yield of natural gene and BatMd fused with SMF was increased 3- and 12-fold, and that of BatMx and BatSMx fused with SMF was increased 20-fold (FIG. 4).

Figure 5:
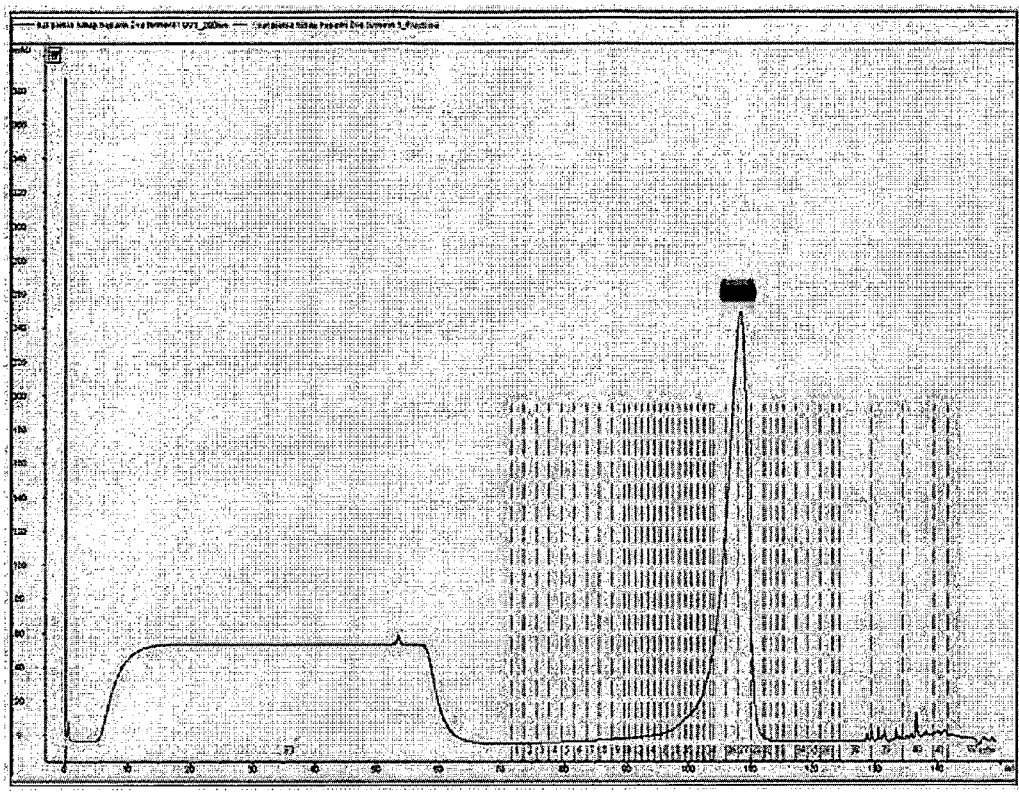

To analyze the amino acid sequence of recombinant batroxobin enzyme, the purified recombinant thrombin-like enzyme was electrophoresed under reducing condition. Batroxobin protein band was cut and then trypsin-in gel digestion was carried out. N-terminal amino acid sequence was analyzed using MALDI-TOF MS analyzer. It was demonstrated that the sequence was the sequence of VIGGDEC-DIN, suggesting that the expressed protein was recombinant batroxobin enzyme (FIG. 5).

Example 7

Comparison of Activity of Recombinant Batroxobin and Natural Batroxobin Enzyme

Figure 6:
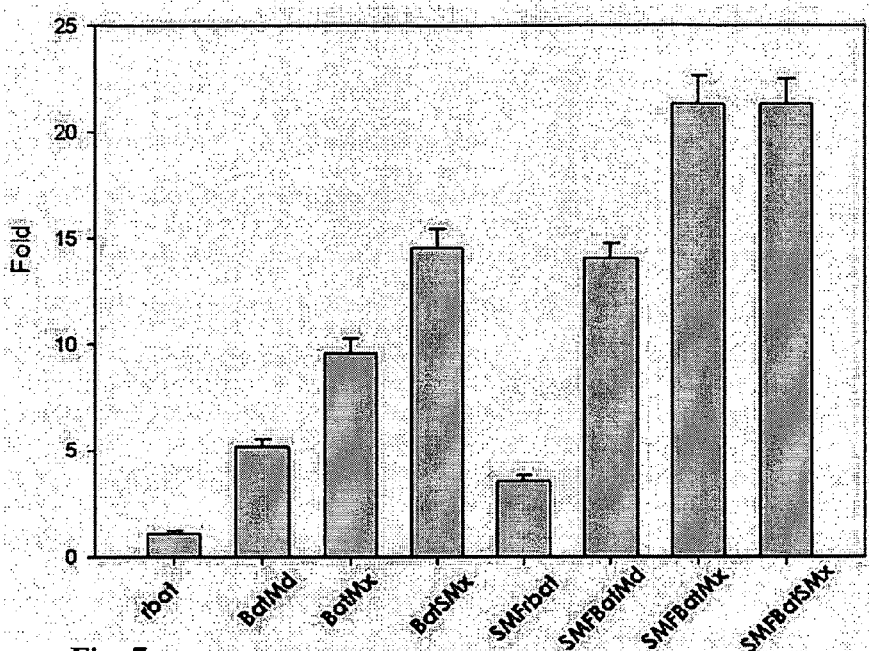
FIG. 6 is a graph for preparation yield of recombinant batroxobins prepared by using various nucleotide sequences.

The catalytic activity of chromogenic substrate (Chromogenix, Instrumentation Laboratory, Spain/Sigma, USA) synthesized to compare the activity of recombinant batroxobin and natural batroxobin enzyme was measured, and the changes of human plasma clotting time was measured by ACL automated blood coagulation instrument (Instrumentation Laboratory, Spain). The catalysis of the synthetic chromogenic substrate caused by contacting recombinant thrombin-like and natural thrombin-like enzyme in the same amount was measured by the change of absorbance at 405 nm. The chromogenic substrate utilized S2238 (H-D-Phe-Pip-Arg-pNA), S2222 (Bz-Ile-Glu-Gly-Arg-pNA), S2288 (H-D-Ile-Pro-Arg-pNA), S2266 (H-D-Val-Leu-Arg-pNA), S2302 (H-D-Pro-Phe-Arg-pNA), T1637 (N-P-Tonsyl-Gly-Pro-Arg-pNA), V2628 (DL-Val-Leu-Arg-pNA), B7632 (N-Benzoyl-Phe-Val-Arg-pNA). Both recombinant protein and natural protein showed the similar pattern in the catalytic activity of thrombin-like enzyme on several synthetic chromogenic substrates, and recombinant batroxobin enzyme demonstrated higher specific activity (FIG. 6a). In FIG. 6a, recombinant protein represented the protein that natural batroxobin gene was expressed in *Pichia pastoris*. Natural batroxobin represented batroxobin enzyme (Pentapharm Ltd, Swiss) purified from venom.

To identify actual blood hemostatic activity of batroxobin enzyme, plasma was isolated from human blood and the same amount of recombinant batroxobin and natural batroxobin enzyme was added to the plasma according to concentration, and then PT (prothrombin time) was measured by ACL automated blood coagulation instrument. The result demonstrated that addition of batroxobin enzyme increased the clotting time in a concentration-dependent manner and the specific activity of recombinant batroxobin was greater than natural batroxobin enzyme like the result of activity measurement using synthetic chromogenic substrate (FIG. 6b).

Example 8

Fibrin Clotting Activity of Recombinant Batroxobin Enzyme

Figure 7:
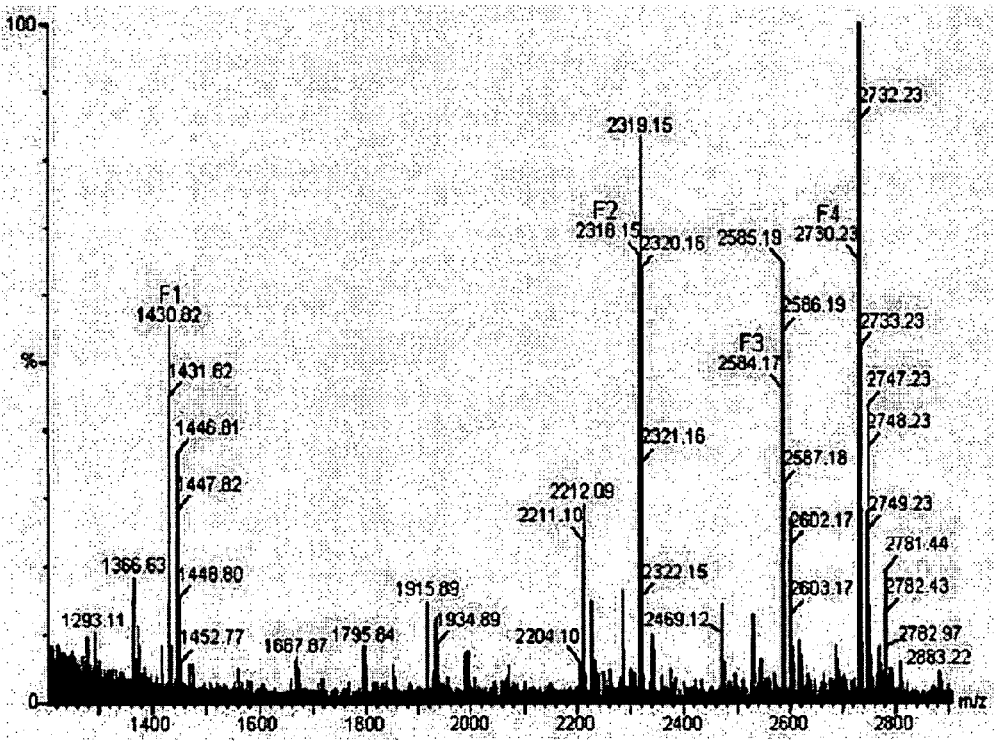
FIG. 7 represents MALDI-TOF analysis of recombinant batroxobins prepared by using a SMFBatSMx gene.
Figure 8:
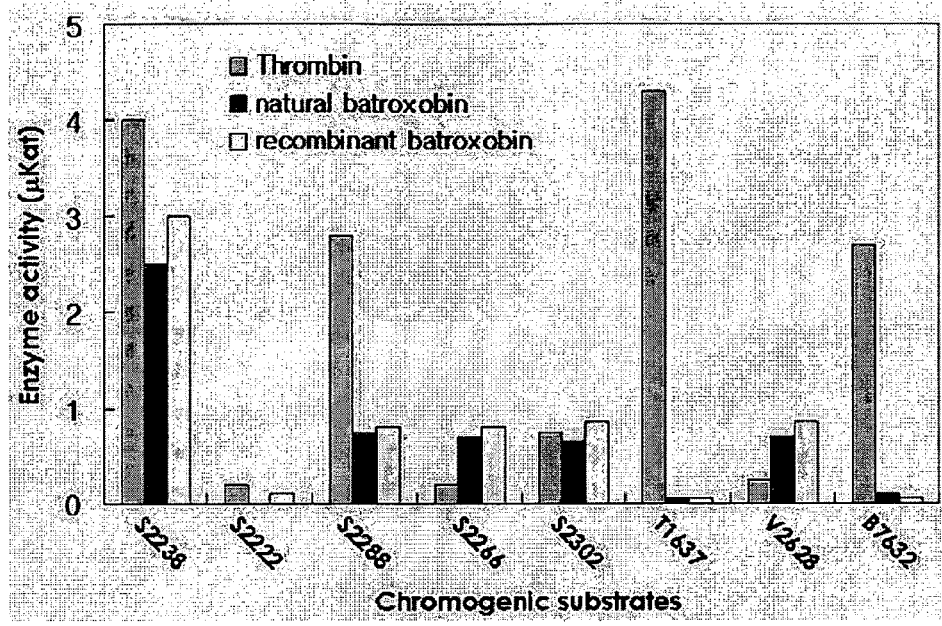
FIGS. 8-9 are graphs to analyze blood coagulation by natural and recombinant batroxobin, respectively.

In vitro fibrin clotting activity test and reverse zymography test were performed with recombinant batroxobin and natural batroxobin enzyme. As shown in FIG. 7, addition of recombinant batroxobin enzyme to 0.5% human fibrinogen solution made insoluble fibrin clot, which was not mixed with water-soluble dye. As shown in FIG. 8a of reverse zymography, insoluble fibrin clot was formed at the location of recombinant enzyme on 0.5% fibrinogen-agar plate and minor bands to be absent in SDS-PAGE and Western blotting were detected. It was demonstrated that these bands were a very small amount of batroxobin formed by partial glycosylation (FIG. 8b).

Example 9

Figure 9:
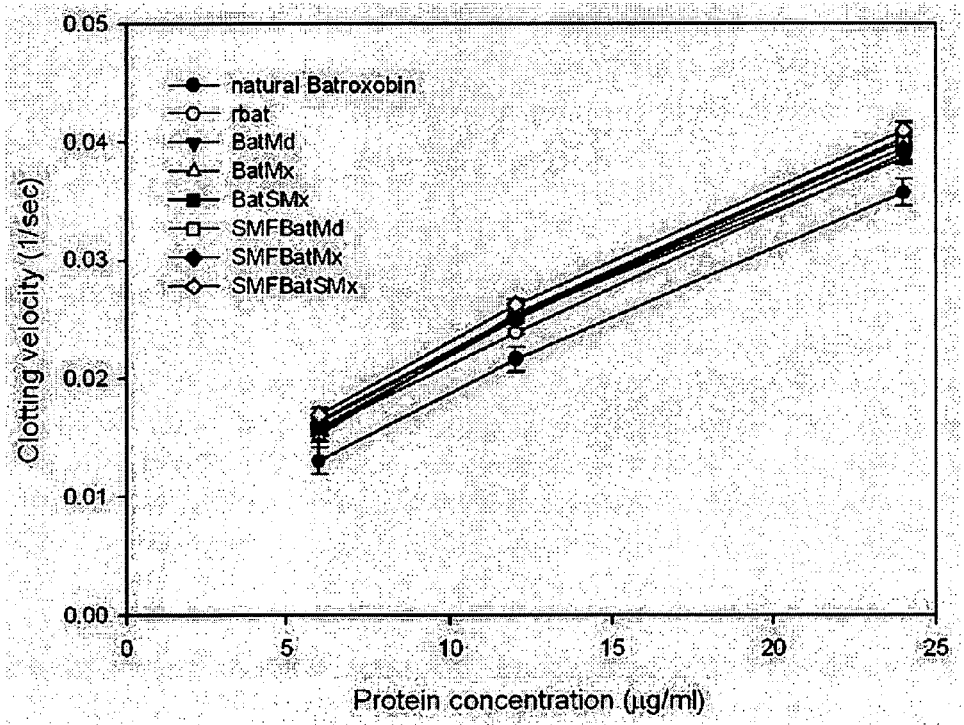

Reduction of Bleeding Time and Whole Blood Coagulation Time by Recombinant Batroxobin Enzyme in Animal Experimental Model To check the clinical application possibility of recombinant batroxobin enzyme, bleeding time reduction was compared with natural batroxobin enzyme in animal experimental model. The about 1 ml sample (1 NIH unit/kg), which is the similar amount like that used in clinical application, was injected on the tail vein of 8-week-old rats (DBL, Korea). After 1.5 hrs, the tail of rats was transected at 5 mm from the tip and the time to stop bleeding was measured with the tail in PBS. The control was injected with only PBS. The each group had 5 animals. As shown in FIG. 9a, the bleeding time of animals injected with recombinant batroxobin or natural batroxobin enzyme was shorter than the control, which was the result of hemostatic activity of batroxobin enzyme. The hemostatic activity of recombinant batroxobin enzyme was better than the natural batroxobin.

In addition, whole blood coagulation time reduction in treated animal model was measured. Recombinant batroxobin and natural batroxobin enzyme (2 NIH unit/kg, respectively) were injected on the tail vein of rats. After 1 hr and 4 hrs, the blood was collected and the whole blood coagulation time was measured. The control was injected with only PBS. Each group had 5 animals. Whole blood coagulation time was measured as follows: The collected blood of 0.5 ml was mixed 10 mM $CaCl_2$ in 1.5 ml eppendorf tube, and then the blood coagulation time was measured with agitation of 2 rpm/min and 45° incline. The whole blood coagulation time of blood treated with batroxobin enzyme was shorter than the control like the result of bleeding time test, and the activity of recombinant batroxobin enzyme was stronger than that of natural batroxobin enzyme (FIG. 9b).

Example 10

Figure 10:
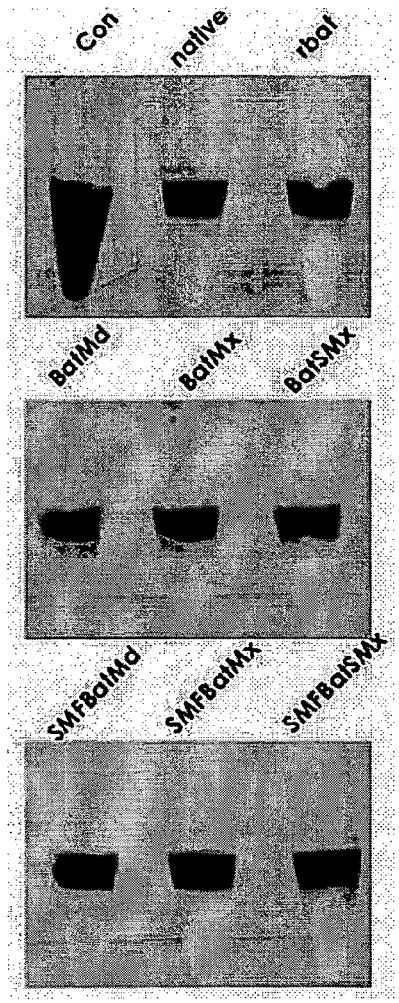
FIG. 10 is a graph representing fibrin coagulation activities by recombinant batroxobins prepared by using various nucleotide sequences.

Changes of PT, APTT and TT by Recombinant Batroxobin Enzyme in Animal Experimental Model As described above, several experiments demonstrated that recombinant batroxobin enzyme has the hemostatic activity to form insoluble fibrin clot like natural batroxobin enzyme. Thus, to investigate whether this recombinant batroxobin enzyme has an influence on other blood coagulation factors, the PT (prothrombin time), APTT (activated partial thromboplastin time) and TT (thrombin time) changes of blood was measured in animal experimental model. Recombinant batroxobin and natural batroxobin enzyme (0.1 NIH unit/kg, respectively) were injected on the tail vein of rats. After 2 hrs, the blood was collected and the plasma was isolated. The changes of PT (FIG. 10a), APTT (FIG. 10b) and TT (FIG. 10c) for each isolated plasma were measured by using automated ACL blood clotting tester. This changes is in vivo assay method to indirectly investigate the changes of several coagulation factors in mammalian blood coagulation system.

The control was the plasma of animal injected with only PBS. Each group had 5 animals. All results were similar, and plasma of animals injected with the sample showed very slight increase at each test. However, the difference was not significant. Based on these results, it is believed that recombinant batroxobin enzyme has no significant influence on other blood coagulation factors compared to the hemostatic activity.

Example 11

Stability Test of Recombinant Batroxobin and Natural Batroxobin Enzyme

Figure 11:
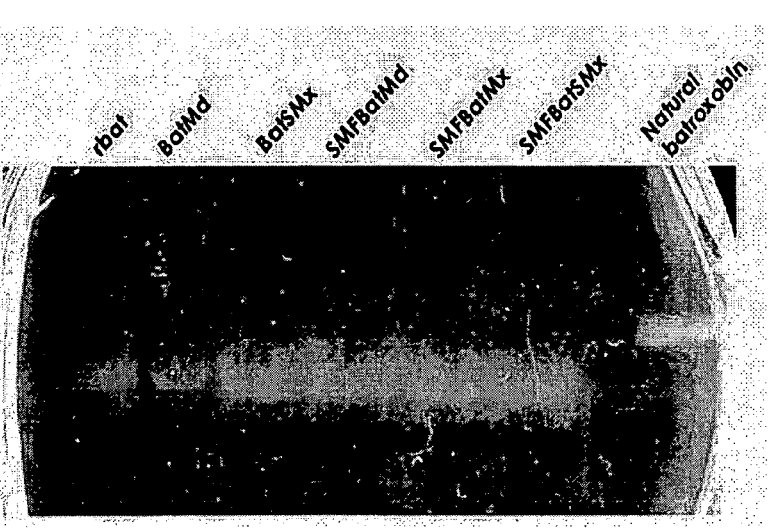
FIGS. 11-12 are reverse zymographies representing fibrin coagulation activities by recombinant batroxobins prepared by using various nucleotide sequences.
Figure 12:
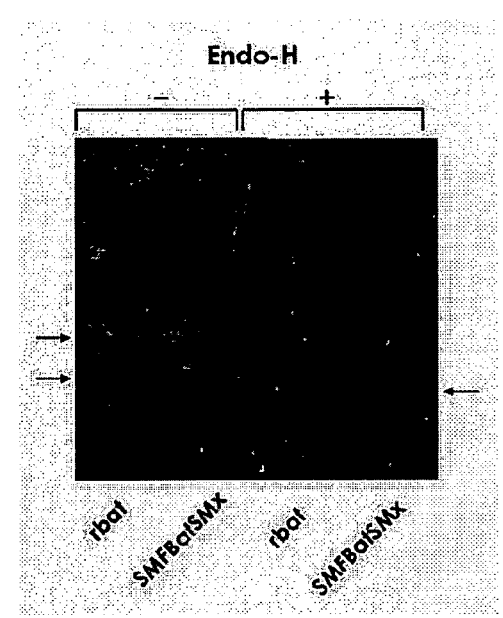
Figure 13:
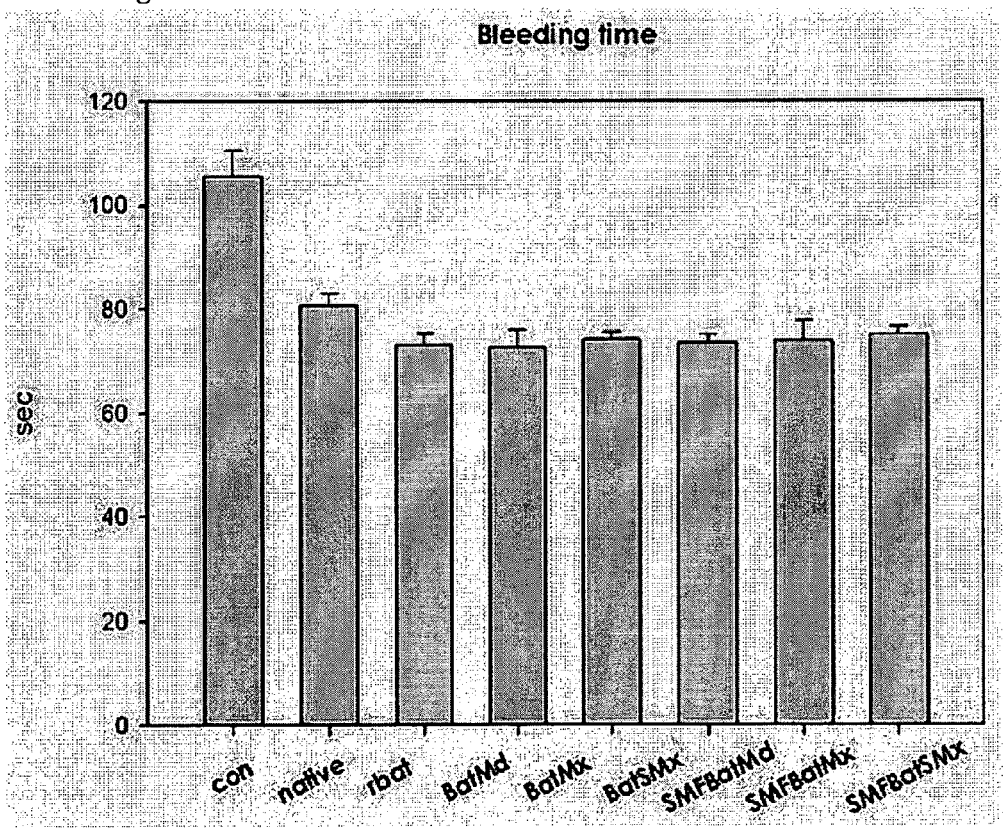
FIGS. 13-14 are graphs representing the activities to reduce bleeding time (FIG. 13) and whole blood clotting time (FIG. 14) in animal model system of recombinant batroxobins.
Figure 14:
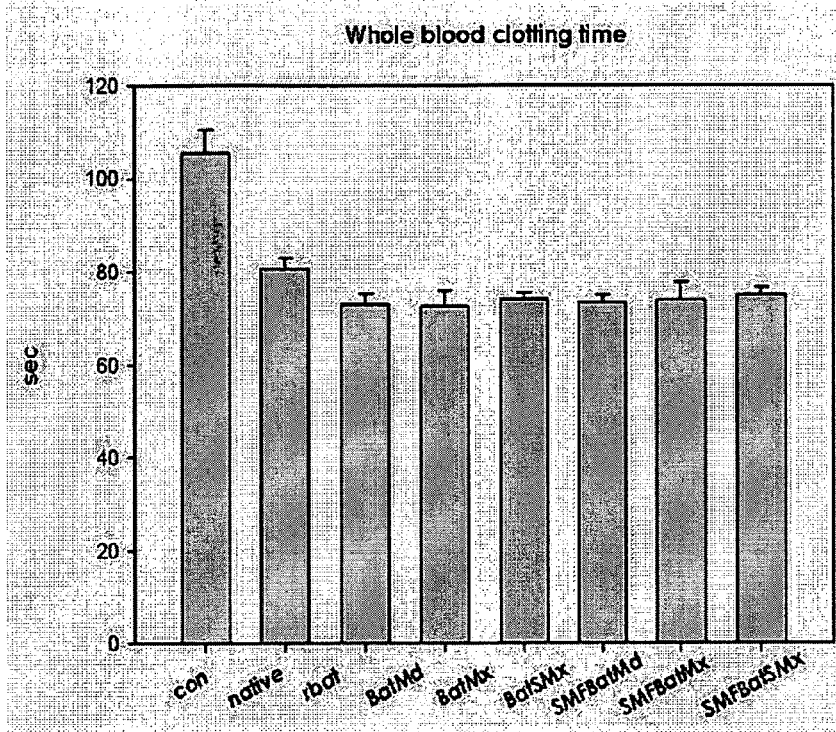
Figure 15:
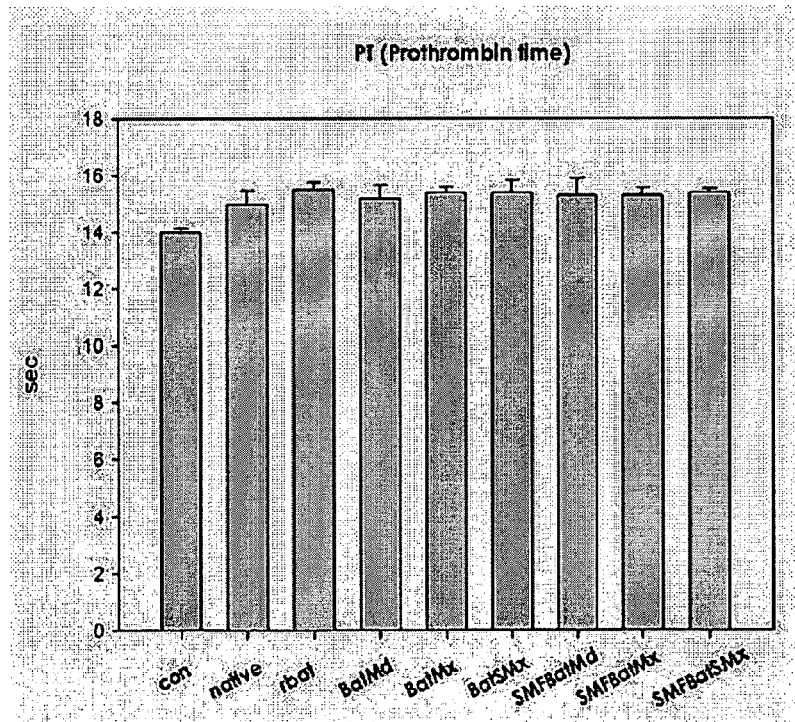
FIGS. 15-17 are graphs measuring PT (prothrombin time, FIG. 15), APTT (activated partial thromboplastin time, FIG. 16) and TT (thrombin time, FIG. 17).
Figure 16:
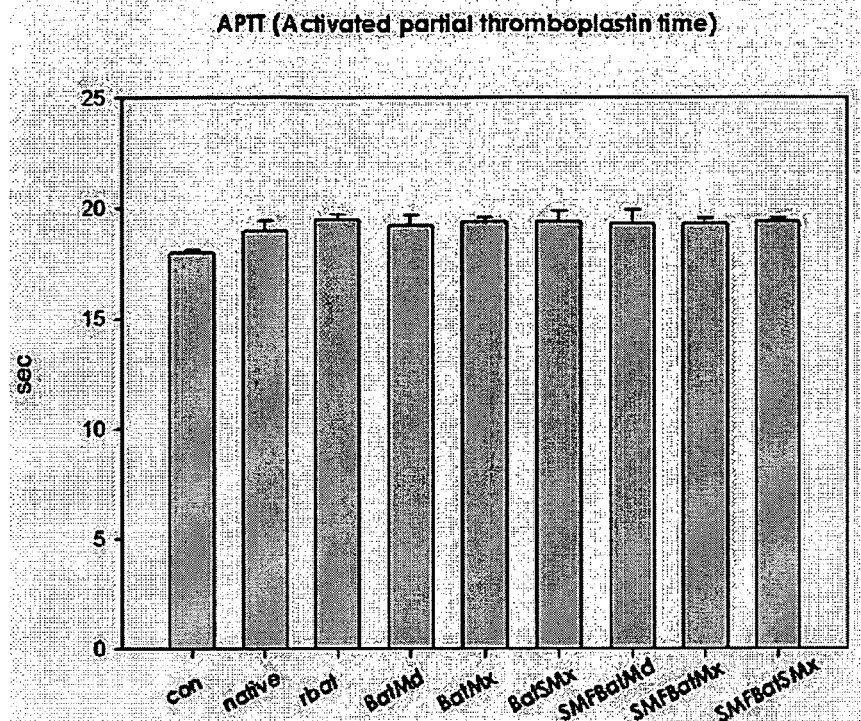
Figure 17:
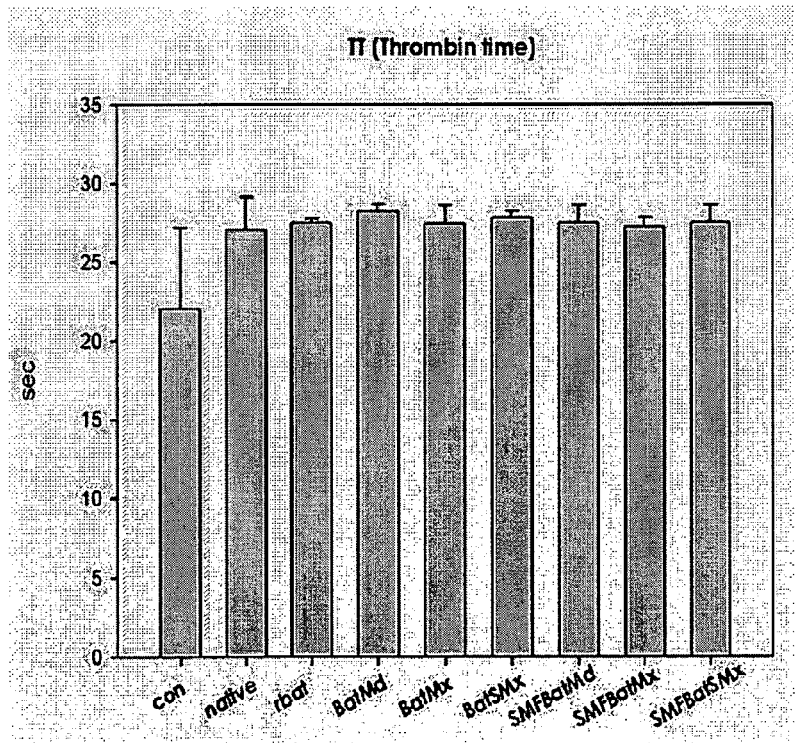
Figure 18:
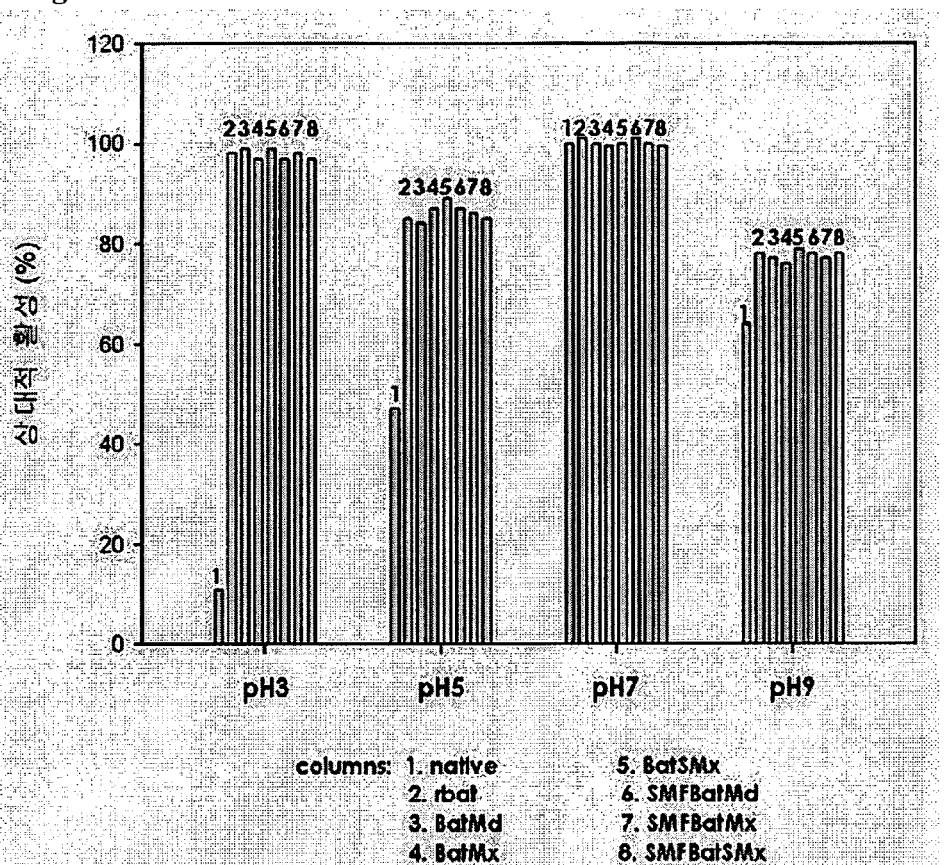
FIG. 18 is a graph for pH stability of recombinant batroxobins.
Figure 19:
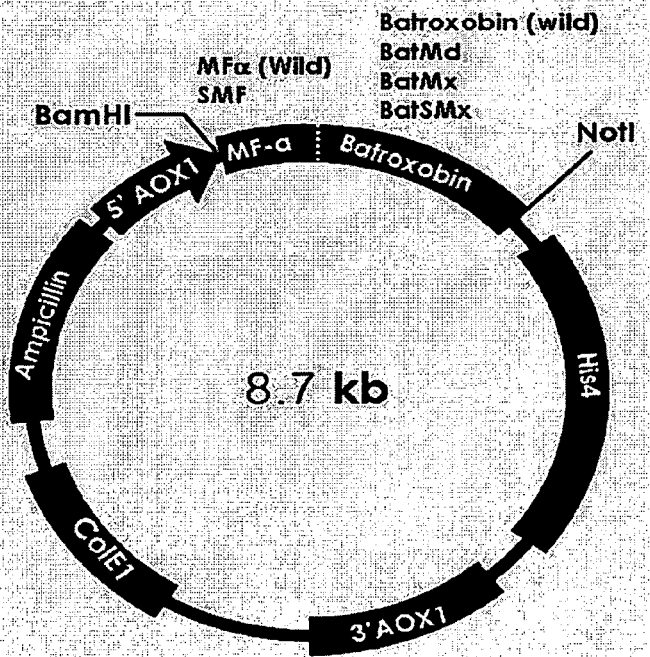
FIG. 19 represents a gene map of the present vector. 5' AOX1, promoter of 5' AOX1 gene; 3' AOX1, promoter of 3' AOX1 gene; Ampicillin, ampicillin-resistant gene; His4, open reading frame of His4 gene; MF-α, α-factor secretion signal sequence; ColE1, pBR322-derived origin; Batroxobin, batroxobin gene.

As the results of the above several experiments for activity comparison, it is believed that the activity of recombinant batroxobin enzyme is stronger than the natural enzyme, which is expected to relate with the protein stability. Thus, the stability of recombinant batroxobin and natural batroxobin enzyme was analyzed by measuring the maintenance of protein activity under several pH conditions. As shown in FIG. 11, recombinant batroxobin enzyme was more stable under each condition. This result is expected to related with the purity of finally isolated and purified protein.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A batroxobin-encoding nucleotide sequence comprising the nucleotide sequence of SEQ ID NO:5 or NO:7.

2. A vector comprising the nucleotide sequences of claim 1 and the α-factor secretion signal peptide-encoding nucleotide sequence of SEQ ID NO:11.

3. A method for preparing a recombinant batroxobin, comprising the steps of:
(a) transforming a host cell using the vector of claim 2; and
(b) culturing the transformed cell to provide the recombinant batroxobin.

* * * * *

SEQUENCE LISTING

```
<160> NUMBER OF SEQ ID NOS: 13

<210> SEQ ID NO 1
<211> LENGTH: 696
<212> TYPE: DNA
<213> ORGANISM: Bothrops atrox
<220> FEATURE:
<221> NAME/KEY: CDS
<222> LOCATION: (1)..(693)

<400> SEQUENCE: 1 gtc att gga ggt gat gaa tgt gac ata aat gaa cat cct ttc ctt gca      48
Val Ile Gly Gly Asp Glu Cys Asp Ile Asn Glu His Pro Phe Leu Ala
1               5                   10                  15 ttc atg tac tac tct ccc cgg tat ttc tgt ggt atg act ttg atc aac      96
Phe Met Tyr Tyr Ser Pro Arg Tyr Phe Cys Gly Met Thr Leu Ile Asn
                20                  25                  30 cag gaa tgg gtg ctg acc gct gca cac tgt aac agg aga ttt atg cgc     144
Gln Glu Trp Val Leu Thr Ala Ala His Cys Asn Arg Arg Phe Met Arg
            35                  40                  45 ata cac ctt ggt aaa cat gcc gga agt gta gca aat tat gat gag gtg     192
Ile His Leu Gly Lys His Ala Gly Ser Val Ala Asn Tyr Asp Glu Val
        50                  55                  60 gta aga tac cca aag gag aag ttc att tgt ccc aat aag aaa aaa aat     240
Val Arg Tyr Pro Lys Glu Lys Phe Ile Cys Pro Asn Lys Lys Lys Asn
65                  70                  75                  80 gtc ata acg gac aag gac att atg ttg atc agg ctg gac aga cct gtc     288
Val Ile Thr Asp Lys Asp Ile Met Leu Ile Arg Leu Asp Arg Pro Val
                85                  90                  95 aaa aac agt gaa cac atc gcg cct ctc agc ttg cct tcc aac cct ccc     336
Lys Asn Ser Glu His Ile Ala Pro Leu Ser Leu Pro Ser Asn Pro Pro
                100                 105                 110
```

```
agt gtg ggc tca gtt tgc cgt att atg gga tgg ggc gca atc aca act          384
Ser Val Gly Ser Val Cys Arg Ile Met Gly Trp Gly Ala Ile Thr Thr
        115                 120                 125 tct gaa gac act tat ccc gat gtc cct cat tgt gct aac att aac ctg          432
Ser Glu Asp Thr Tyr Pro Asp Val Pro His Cys Ala Asn Ile Asn Leu
130                 135                 140 ttc aat aat acg gtg tgt cgt gaa gct tac aat ggg ttg ccg gcg aaa          480
Phe Asn Asn Thr Val Cys Arg Glu Ala Tyr Asn Gly Leu Pro Ala Lys
145                 150                 155                 160 aca ttg tgt gca ggt gtc ctg caa gga ggc ata gat aca tgt ggg ggt          528
Thr Leu Cys Ala Gly Val Leu Gln Gly Gly Ile Asp Thr Cys Gly Gly
        165                 170                 175 gac tct ggg gga ccc ctc atc tgt aat gga caa ttc cag ggc att tta          576
Asp Ser Gly Gly Pro Leu Ile Cys Asn Gly Gln Phe Gln Gly Ile Leu
        180                 185                 190 tct tgg gga agt gat ccc tgt gcc gaa ccg cgt aag cct gcc ttc tac          624
Ser Trp Gly Ser Asp Pro Cys Ala Glu Pro Arg Lys Pro Ala Phe Tyr
        195                 200                 205 acc aag gtc ttt gat tat ctt ccc tgg atc cag agc att att gca gga          672
Thr Lys Val Phe Asp Tyr Leu Pro Trp Ile Gln Ser Ile Ile Ala Gly
210                 215                 220 aat aaa act gcg act tgc ccg tga                                          696
Asn Lys Thr Ala Thr Cys Pro
225                 230
```

<210> SEQ ID NO 2
<211> LENGTH: 231
<212> TYPE: PRT
<213> ORGANISM: Bothrops atrox

<400> SEQUENCE: 2

```
Val Ile Gly Gly Asp Glu Cys Asp Ile Asn Glu His Pro Phe Leu Ala
1               5                   10                  15

Phe Met Tyr Tyr Ser Pro Arg Tyr Phe Cys Gly Met Thr Leu Ile Asn
            20                  25                  30

Gln Glu Trp Val Leu Thr Ala Ala His Cys Asn Arg Arg Phe Met Arg
        35                  40                  45

Ile His Leu Gly Lys His Ala Gly Ser Val Ala Asn Tyr Asp Glu Val
    50                  55                  60

Val Arg Tyr Pro Lys Glu Lys Phe Ile Cys Pro Asn Lys Lys Asn
65                  70                  75                  80

Val Ile Thr Asp Lys Asp Ile Met Leu Ile Arg Leu Asp Arg Pro Val
                85                  90                  95

Lys Asn Ser Glu His Ile Ala Pro Leu Ser Leu Pro Ser Asn Pro Pro
            100                 105                 110

Ser Val Gly Ser Val Cys Arg Ile Met Gly Trp Gly Ala Ile Thr Thr
        115                 120                 125

Ser Glu Asp Thr Tyr Pro Asp Val Pro His Cys Ala Asn Ile Asn Leu
    130                 135                 140

Phe Asn Asn Thr Val Cys Arg Glu Ala Tyr Asn Gly Leu Pro Ala Lys
145                 150                 155                 160

Thr Leu Cys Ala Gly Val Leu Gln Gly Gly Ile Asp Thr Cys Gly Gly
                165                 170                 175

Asp Ser Gly Gly Pro Leu Ile Cys Asn Gly Gln Phe Gln Gly Ile Leu
            180                 185                 190

Ser Trp Gly Ser Asp Pro Cys Ala Glu Pro Arg Lys Pro Ala Phe Tyr
        195                 200                 205

Thr Lys Val Phe Asp Tyr Leu Pro Trp Ile Gln Ser Ile Ile Ala Gly
```

Asn Lys Thr Ala Thr Cys Pro
225             230

<210> SEQ ID NO 3
<211> LENGTH: 696
<212> TYPE: DNA
<213> ORGANISM: Artificial Sequence
<220> FEATURE:
<223> OTHER INFORMATION: Synthetic Construct; BatMd
<220> FEATURE:
<221> NAME/KEY: CDS
<222> LOCATION: (1)..(693)

<400> SEQUENCE: 3

```
gtc att gga ggt gat gaa tgt gac ata aat gaa cat cct ttc ctt gca      48
Val Ile Gly Gly Asp Glu Cys Asp Ile Asn Glu His Pro Phe Leu Ala
1               5                  10                  15 ttc atg tac tac tct cct aga tat ttc tgt ggt atg act ttg atc aac      96
Phe Met Tyr Tyr Ser Pro Arg Tyr Phe Cys Gly Met Thr Leu Ile Asn
            20                  25                  30 cag gaa tgg gtg ctg acc gct gca cac tgt aac agg aga ttt atg aga     144
Gln Glu Trp Val Leu Thr Ala Ala His Cys Asn Arg Arg Phe Met Arg
        35                  40                  45 att cac ttg ggt aaa cat gcc gga agt gta gca aat tat gat gag gtg     192
Ile His Leu Gly Lys His Ala Gly Ser Val Ala Asn Tyr Asp Glu Val
    50                  55                  60 gta aga tac cca aag gag aag ttc att tgt ccc aat aag aaa aaa aat     240
Val Arg Tyr Pro Lys Glu Lys Phe Ile Cys Pro Asn Lys Lys Lys Asn
65                  70                  75                  80 gtc ata acg gac aag gac att atg ttg atc agg ctg gac aga cct gtc     288
Val Ile Thr Asp Lys Asp Ile Met Leu Ile Arg Leu Asp Arg Pro Val
                85                  90                  95 aaa aac agt gaa cac atc gct cct ttg tct ttg cct tcc aac cct ccc     336
Lys Asn Ser Glu His Ile Ala Pro Leu Ser Leu Pro Ser Asn Pro Pro
            100                 105                 110 agt gtg ggc tca gtt tgc cgt att atg gga tgg ggc gca atc aca act     384
Ser Val Gly Ser Val Cys Arg Ile Met Gly Trp Gly Ala Ile Thr Thr
        115                 120                 125 tct gaa gac act tat ccc gat gtc cct cat tgt gct aac att aac ctg     432
Ser Glu Asp Thr Tyr Pro Asp Val Pro His Cys Ala Asn Ile Asn Leu
    130                 135                 140 ttc aat aat acg gtg tgt cgt gaa gct tac aat ggt ttg cca gct aaa     480
Phe Asn Asn Thr Val Cys Arg Glu Ala Tyr Asn Gly Leu Pro Ala Lys
145                 150                 155                 160 aca ttg tgt gca ggt gtc ttg caa gga ggt att gat aca tgt ggt ggt     528
Thr Leu Cys Ala Gly Val Leu Gln Gly Gly Ile Asp Thr Cys Gly Gly
                165                 170                 175 gac tct ggt gga cct ttg atc tgt aat gga caa ttc cag ggt att ttg     576
Asp Ser Gly Gly Pro Leu Ile Cys Asn Gly Gln Phe Gln Gly Ile Leu
            180                 185                 190 tct tgg gga tct gat cct tgt gcc gaa cca aga aag cct gcc ttc tac     624
Ser Trp Gly Ser Asp Pro Cys Ala Glu Pro Arg Lys Pro Ala Phe Tyr
        195                 200                 205 acc aag gtc ttt gat tat ttg cct tgg atc cag tct att att gca gga     672
Thr Lys Val Phe Asp Tyr Leu Pro Trp Ile Gln Ser Ile Ile Ala Gly
    210                 215                 220 aat aaa act gct act tgc cca tga                                     696
Asn Lys Thr Ala Thr Cys Pro
225                 230
```

<210> SEQ ID NO 4

```
<211> LENGTH: 231
<212> TYPE: PRT
<213> ORGANISM: Artificial Sequence
<220> FEATURE:
<223> OTHER INFORMATION: Synthetic Construct

<400> SEQUENCE: 4

Val Ile Gly Gly Asp Glu Cys Asp Ile Asn Glu His Pro Phe Leu Ala
1               5                   10                  15

Phe Met Tyr Tyr Ser Pro Arg Tyr Phe Cys Gly Met Thr Leu Ile Asn
            20                  25                  30

Gln Glu Trp Val Leu Thr Ala Ala His Cys Asn Arg Arg Phe Met Arg
        35                  40                  45

Ile His Leu Gly Lys His Ala Gly Ser Val Ala Asn Tyr Asp Glu Val
    50                  55                  60

Val Arg Tyr Pro Lys Glu Lys Phe Ile Cys Pro Asn Lys Lys Lys Asn
65                  70                  75                  80

Val Ile Thr Asp Lys Asp Ile Met Leu Ile Arg Leu Asp Arg Pro Val
                85                  90                  95

Lys Asn Ser Glu His Ile Ala Pro Leu Ser Leu Pro Ser Asn Pro Pro
            100                 105                 110

Ser Val Gly Ser Val Cys Arg Ile Met Gly Trp Gly Ala Ile Thr Thr
        115                 120                 125

Ser Glu Asp Thr Tyr Pro Asp Val Pro His Cys Ala Asn Ile Asn Leu
    130                 135                 140

Phe Asn Asn Thr Val Cys Arg Glu Ala Tyr Asn Gly Leu Pro Ala Lys
145                 150                 155                 160

Thr Leu Cys Ala Gly Val Leu Gln Gly Gly Ile Asp Thr Cys Gly Gly
                165                 170                 175

Asp Ser Gly Gly Pro Leu Ile Cys Asn Gly Gln Phe Gln Gly Ile Leu
            180                 185                 190

Ser Trp Gly Ser Asp Pro Cys Ala Glu Pro Arg Lys Pro Ala Phe Tyr
        195                 200                 205

Thr Lys Val Phe Asp Tyr Leu Pro Trp Ile Gln Ser Ile Ile Ala Gly
    210                 215                 220

Asn Lys Thr Ala Thr Cys Pro
225                 230

<210> SEQ ID NO 5
<211> LENGTH: 696
<212> TYPE: DNA
<213> ORGANISM: Artificial Sequence
<220> FEATURE:
<223> OTHER INFORMATION: Synthetic Construct; BatMx
<220> FEATURE:
<221> NAME/KEY: CDS
<222> LOCATION: (1)..(693)

<400> SEQUENCE: 5 gtc att gga ggt gat gaa tgt gac att aat gaa cat cct ttc ttg gca      48
Val Ile Gly Gly Asp Glu Cys Asp Ile Asn Glu His Pro Phe Leu Ala
1               5                   10                  15 ttc atg tac tac tct cct aga tat ttc tgt ggt atg act ttg atc aac      96
Phe Met Tyr Tyr Ser Pro Arg Tyr Phe Cys Gly Met Thr Leu Ile Asn
            20                  25                  30 cag gaa tgg gtt ttg acc gct gca cac tgt aac aga aga ttt atg aga     144
Gln Glu Trp Val Leu Thr Ala Ala His Cys Asn Arg Arg Phe Met Arg
        35                  40                  45 att cac ttg ggt aaa cat gcc gga tct gtt gca aat tat gat gag gtt     192
Ile His Leu Gly Lys His Ala Gly Ser Val Ala Asn Tyr Asp Glu Val
```

```
              50                  55                  60
gtt aga tac cca aag gag aag ttc att tgt cct aat aag aaa aaa aat    240
Val Arg Tyr Pro Lys Glu Lys Phe Ile Cys Pro Asn Lys Lys Lys Asn
 65                  70                  75                  80 gtc att act gac aag gac att atg ttg atc aga ttg gac aga cct gtc    288
Val Ile Thr Asp Lys Asp Ile Met Leu Ile Arg Leu Asp Arg Pro Val
                 85                  90                  95 aaa aac tct gaa cac atc gct cct ttg tct ttg cct tct aac cct cct    336
Lys Asn Ser Glu His Ile Ala Pro Leu Ser Leu Pro Ser Asn Pro Pro
            100                 105                 110 tct gtt ggt tct gtt tgc aga att atg gga tgg ggt gca atc aca act    384
Ser Val Gly Ser Val Cys Arg Ile Met Gly Trp Gly Ala Ile Thr Thr
        115                 120                 125 tct gaa gac act tat cct gat gtc cct cat tgt gct aac att aac ttg    432
Ser Glu Asp Thr Tyr Pro Asp Val Pro His Cys Ala Asn Ile Asn Leu
130                 135                 140 ttc aat aat act gtt tgt aga gaa gct tac aat ggt ttg cca gct aaa    480
Phe Asn Asn Thr Val Cys Arg Glu Ala Tyr Asn Gly Leu Pro Ala Lys
145                 150                 155                 160 aca ttg tgt gca ggt gtc ttg caa gga ggt att gat aca tgt ggt ggt    528
Thr Leu Cys Ala Gly Val Leu Gln Gly Gly Ile Asp Thr Cys Gly Gly
                165                 170                 175 gac tct ggt gga cct ttg atc tgt aat gga caa ttc cag ggt att ttg    576
Asp Ser Gly Gly Pro Leu Ile Cys Asn Gly Gln Phe Gln Gly Ile Leu
            180                 185                 190 tct tgg gga tct gat cct tgt gcc gaa cca aga aag cct gcc ttc tac    624
Ser Trp Gly Ser Asp Pro Cys Ala Glu Pro Arg Lys Pro Ala Phe Tyr
        195                 200                 205 acc aag gtc ttt gat tat ttg cct tgg atc cag tct att att gca gga    672
Thr Lys Val Phe Asp Tyr Leu Pro Trp Ile Gln Ser Ile Ile Ala Gly
210                 215                 220 aat aaa act gct act tgc cca tga                                    696
Asn Lys Thr Ala Thr Cys Pro
225                 230

<210> SEQ ID NO 6
<211> LENGTH: 231
<212> TYPE: PRT
<213> ORGANISM: Artificial Sequence
<220> FEATURE:
<223> OTHER INFORMATION: Synthetic Construct

<400> SEQUENCE: 6

Val Ile Gly Gly Asp Glu Cys Asp Ile Asn Glu His Pro Phe Leu Ala
 1               5                  10                  15

Phe Met Tyr Tyr Ser Pro Arg Tyr Phe Cys Gly Met Thr Leu Ile Asn
                 20                  25                  30

Gln Glu Trp Val Leu Thr Ala Ala His Cys Asn Arg Arg Phe Met Arg
            35                  40                  45

Ile His Leu Gly Lys His Ala Gly Ser Val Ala Asn Tyr Asp Glu Val
        50                  55                  60

Val Arg Tyr Pro Lys Glu Lys Phe Ile Cys Pro Asn Lys Lys Lys Asn
 65                  70                  75                  80

Val Ile Thr Asp Lys Asp Ile Met Leu Ile Arg Leu Asp Arg Pro Val
                 85                  90                  95

Lys Asn Ser Glu His Ile Ala Pro Leu Ser Leu Pro Ser Asn Pro Pro
            100                 105                 110

Ser Val Gly Ser Val Cys Arg Ile Met Gly Trp Gly Ala Ile Thr Thr
        115                 120                 125
```

```
Ser Glu Asp Thr Tyr Pro Asp Val Pro His Cys Ala Asn Ile Asn Leu
    130                 135                 140

Phe Asn Asn Thr Val Cys Arg Glu Ala Tyr Asn Gly Leu Pro Ala Lys
145                 150                 155                 160

Thr Leu Cys Ala Gly Val Leu Gln Gly Gly Ile Asp Thr Cys Gly Gly
                165                 170                 175

Asp Ser Gly Gly Pro Leu Ile Cys Asn Gly Gln Phe Gln Gly Ile Leu
            180                 185                 190

Ser Trp Gly Ser Asp Pro Cys Ala Glu Pro Arg Lys Pro Ala Phe Tyr
        195                 200                 205

Thr Lys Val Phe Asp Tyr Leu Pro Trp Ile Gln Ser Ile Ile Ala Gly
    210                 215                 220

Asn Lys Thr Ala Thr Cys Pro
225                 230

<210> SEQ ID NO 7
<211> LENGTH: 696
<212> TYPE: DNA
<213> ORGANISM: Artificial Sequence
<220> FEATURE:
<223> OTHER INFORMATION: Synthetic Construct;BatSMx
<220> FEATURE:
<221> NAME/KEY: CDS
<222> LOCATION: (1)..(693)

<400> SEQUENCE: 7 gtt att ggt ggt gat gaa tgt gat att aat gaa cat cca ttt ttg gca      48
Val Ile Gly Gly Asp Glu Cys Asp Ile Asn Glu His Pro Phe Leu Ala
1               5                   10                  15 ttt atg tac tac tct cca aga tac ttt tgt ggt atg act ttg att aac      96
Phe Met Tyr Tyr Ser Pro Arg Tyr Phe Cys Gly Met Thr Leu Ile Asn
                20                  25                  30 caa gaa tgg gtt ttg act gca gca cat tgt aac aga aga ttt atg aga     144
Gln Glu Trp Val Leu Thr Ala Ala His Cys Asn Arg Arg Phe Met Arg
            35                  40                  45 att cat ttg ggt aag cat gca ggt tct gtt gca aat tac gat gaa gtt     192
Ile His Leu Gly Lys His Ala Gly Ser Val Ala Asn Tyr Asp Glu Val
        50                  55                  60 gtt aga tac cca aag gaa aag ttt att tgt cca aat aag aag aag aat     240
Val Arg Tyr Pro Lys Glu Lys Phe Ile Cys Pro Asn Lys Lys Lys Asn
65                  70                  75                  80 gtt att act gat aag gat att atg ttg att aga ttg gat aga cca gtt     288
Val Ile Thr Asp Lys Asp Ile Met Leu Ile Arg Leu Asp Arg Pro Val
                85                  90                  95 aag aac tct gaa cat att gca cca ttg tct ttg cca tct aac cca cca     336
Lys Asn Ser Glu His Ile Ala Pro Leu Ser Leu Pro Ser Asn Pro Pro
            100                 105                 110 tct gtt ggt tct gtt tgt aga att atg ggt tgg ggt gca att act act     384
Ser Val Gly Ser Val Cys Arg Ile Met Gly Trp Gly Ala Ile Thr Thr
        115                 120                 125 tct gaa gat act tac cca gat gtt cca cat tgt gca aac att aac ttg     432
Ser Glu Asp Thr Tyr Pro Asp Val Pro His Cys Ala Asn Ile Asn Leu
    130                 135                 140 ttt aat aat act gtt tgt aga gaa gca tac aat ggt ttg cca gca aag     480
Phe Asn Asn Thr Val Cys Arg Glu Ala Tyr Asn Gly Leu Pro Ala Lys
145                 150                 155                 160 act ttg tgt gca ggt gtt ttg caa ggt ggt att gat act tgt ggt ggt     528
Thr Leu Cys Ala Gly Val Leu Gln Gly Gly Ile Asp Thr Cys Gly Gly
                165                 170                 175 gat tct ggt ggt cca ttg att tgt aat ggt caa ttt caa ggt att ttg     576
Asp Ser Gly Gly Pro Leu Ile Cys Asn Gly Gln Phe Gln Gly Ile Leu
```

```
                  180                 185                 190
tct tgg ggt tct gat cca tgt gca gaa cca aga aag cca gca ttt tac       624
Ser Trp Gly Ser Asp Pro Cys Ala Glu Pro Arg Lys Pro Ala Phe Tyr
        195                 200                 205 act aag gtt ttt gat tac ttg cca tgg att caa tct att att gca ggt       672
Thr Lys Val Phe Asp Tyr Leu Pro Trp Ile Gln Ser Ile Ile Ala Gly
    210                 215                 220 aat aag act gca act tgt cca taa                                       696
Asn Lys Thr Ala Thr Cys Pro
225                 230
```

```
<210> SEQ ID NO 8
<211> LENGTH: 231
<212> TYPE: PRT
<213> ORGANISM: Artificial Sequence
<220> FEATURE:
<223> OTHER INFORMATION: Synthetic Construct

<400> SEQUENCE: 8

Val Ile Gly Gly Asp Glu Cys Asp Ile Asn Glu His Pro Phe Leu Ala
1               5                   10                  15

Phe Met Tyr Tyr Ser Pro Arg Tyr Phe Cys Gly Met Thr Leu Ile Asn
            20                  25                  30

Gln Glu Trp Val Leu Thr Ala Ala His Cys Asn Arg Arg Phe Met Arg
        35                  40                  45

Ile His Leu Gly Lys His Ala Gly Ser Val Ala Asn Tyr Asp Glu Val
    50                  55                  60

Val Arg Tyr Pro Lys Glu Lys Phe Ile Cys Pro Asn Lys Lys Lys Asn
65                  70                  75                  80

Val Ile Thr Asp Lys Asp Ile Met Leu Ile Arg Leu Asp Arg Pro Val
                85                  90                  95

Lys Asn Ser Glu His Ile Ala Pro Leu Ser Leu Pro Ser Asn Pro Pro
            100                 105                 110

Ser Val Gly Ser Val Cys Arg Ile Met Gly Trp Gly Ala Ile Thr Thr
        115                 120                 125

Ser Glu Asp Thr Tyr Pro Asp Val Pro His Cys Ala Asn Ile Asn Leu
    130                 135                 140

Phe Asn Asn Thr Val Cys Arg Glu Ala Tyr Asn Gly Leu Pro Ala Lys
145                 150                 155                 160

Thr Leu Cys Ala Gly Val Leu Gln Gly Gly Ile Asp Thr Cys Gly Gly
                165                 170                 175

Asp Ser Gly Gly Pro Leu Ile Cys Asn Gly Gln Phe Gln Gly Ile Leu
            180                 185                 190

Ser Trp Gly Ser Asp Pro Cys Ala Glu Pro Arg Lys Pro Ala Phe Tyr
        195                 200                 205

Thr Lys Val Phe Asp Tyr Leu Pro Trp Ile Gln Ser Ile Ile Ala Gly
    210                 215                 220

Asn Lys Thr Ala Thr Cys Pro
225                 230

<210> SEQ ID NO 9
<211> LENGTH: 255
<212> TYPE: DNA
<213> ORGANISM: Saccharomyces cerevisiae
<220> FEATURE:
<221> NAME/KEY: CDS
<222> LOCATION: (1)..(255)

<400> SEQUENCE: 9
```

```
atg aga ttt cct tca att ttt act gca gtt tta ttc gca gca tcc tcc      48
Met Arg Phe Pro Ser Ile Phe Thr Ala Val Leu Phe Ala Ala Ser Ser
1               5                   10                  15 gca tta gct gct cca gtc aac act aca aca gaa gat gaa acg gca caa      96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
50                  55                  60 ttt ata aat act act att gcc agc att gct gct aaa gaa gaa ggg gta     240
Phe Ile Asn Thr Thr Ile Ala Ser Ile Ala Ala Lys Glu Glu Gly Val
65                  70                  75                  80 tct ctc gag aaa aga                                                  255
Ser Leu Glu Lys Arg
                85

<210> SEQ ID NO 10
<211> LENGTH: 85
<212> TYPE: PRT
<213> ORGANISM: Saccharomyces cerevisiae

<400> SEQUENCE: 10

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Glu Lys Arg
                85

<210> SEQ ID NO 11
<211> LENGTH: 255
<212> TYPE: DNA
<213> ORGANISM: Artificial Sequence
<220> FEATURE:
<223> OTHER INFORMATION: Synthetic Construct;SMF
<220> FEATURE:
<221> NAME/KEY: CDS
<222> LOCATION: (1)..(255)

<400> SEQUENCE: 11 atg aga ttt cca tct att ttt act gca gtt ttg ttt gca gca tct tct      48
Met Arg Phe Pro Ser Ile Phe Thr Ala Val Leu Phe Ala Ala Ser Ser
1               5                   10                  15 gca ttg gca gca cca gtt aac act act act gaa gat gaa act gca caa      96
Ala Leu Ala Ala Pro Val Asn Thr Thr Thr Glu Asp Glu Thr Ala Gln
            20                  25                  30 att cca gca gaa gca gtt att ggt tac tct gat ttg gaa ggt gat ttt     144
Ile Pro Ala Glu Ala Val Ile Gly Tyr Ser Asp Leu Glu Gly Asp Phe
        35                  40                  45 gat gtt gct gtt ttg cca ttt tct aac tct act aat aac ggt ttg ttg     192
Asp Val Ala Val Leu Pro Phe Ser Asn Ser Thr Asn Asn Gly Leu Leu
50                  55                  60 ttt att aat act act att gca tct att gca gca aag gaa gaa ggt gtt     240
```

```
Phe Ile Asn Thr Thr Ile Ala Ser Ile Ala Ala Lys Glu Glu Gly Val
 65                  70                  75                  80 tct ttg gaa aaa aga                                                    255
Ser Leu Glu Lys Arg
                85

<210> SEQ ID NO 12
<211> LENGTH: 85
<212> TYPE: PRT
<213> ORGANISM: Artificial Sequence
<220> FEATURE:
<223> OTHER INFORMATION: Synthetic Construct

<400> SEQUENCE: 12

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
 65                  70                  75                  80

Ser Leu Glu Lys Arg
                85

<210> SEQ ID NO 13
<211> LENGTH: 274
<212> TYPE: DNA
<213> ORGANISM: Artificial Sequence
<220> FEATURE:
<223> OTHER INFORMATION: Synthetic Construct; cloning cassette for SMF

<400> SEQUENCE: 13
ggatccaaac gatgagattt ccatctattt ttactgcagt tttgtttgca gcatcttctg      60
cattggcagc accagttaac actactactg aagatgaaac tgcacaaatt ccagcagaag     120
cagttattgg ttactctgat ttggaaggtg attttgatgt tgctgttttg ccattttcta     180
actctactaa taacggtttg ttgtttatta atactactat tgcatctatt gcagcaaagg     240
aagaaggtgt ttctttggaa aaaagagcgg ccgc                                 274
```